(12) United States Patent
Bentley et al.

(10) Patent No.: US 9,284,411 B2
(45) Date of Patent: Mar. 15, 2016

(54) POLYOXAZOLINES WITH INERT TERMINATING GROUPS, POLYOXAZOLINES PREPARED FROM PROTECTED INITIATING GROUPS AND RELATED COMPOUNDS

(71) Applicant: SERINA THERAPEUTICS, INC., Huntsville, AL (US)

(72) Inventors: Michael D Bentley, Huntsville, AL (US); J Milton Harris, Huntsville, AL (US); Kunsang Yoon, Madison, AL (US); Michael Reif, Munich (DE); Rainer Jordan, Munich (DE)

(73) Assignee: Serina Therapeutics, Inc., Huntsville, AL (US)

( * ) Notice: Subject to any disclaimer, the term of this patent is extended or adjusted under 35 U.S.C. 154(b) by 0 days.

(21) Appl. No.: 14/537,516

(22) Filed: Nov. 10, 2014

(65) Prior Publication Data
US 2015/0080538 A1 Mar. 19, 2015

Related U.S. Application Data

(63) Continuation of application No. 13/003,306, filed as application No. PCT/US2009/050286 on Jul. 10, 2009, now Pat. No. 8,883,211.

(60) Provisional application No. 61/079,799, filed on Jul. 10, 2008.

(51) Int. Cl.
| | | |
|---|---|---|
| *A61K 9/14* | (2006.01) | |
| *C08G 73/02* | (2006.01) | |
| *A61K 9/127* | (2006.01) | |
| *C08L 79/02* | (2006.01) | |

(52) U.S. Cl.
CPC .......... *C08G 73/0233* (2013.01); *A61K 9/1272* (2013.01); *C08L 79/02* (2013.01)

(58) Field of Classification Search
None
See application file for complete search history.

(56) References Cited

U.S. PATENT DOCUMENTS

| | | | |
|---|---|---|---|
| 4,001,068 A | 1/1977 | Robinson | |
| 4,131,724 A | 12/1978 | Radlmann | |
| 4,271,230 A | 6/1981 | Sakano | |
| 4,436,789 A | 3/1984 | Davis | |
| 4,464,438 A | 8/1984 | Lu | |
| 4,525,495 A | 6/1985 | Dorman | |
| 4,593,103 A | 6/1986 | Johnson | |
| 4,622,353 A | 11/1986 | Weiss | |
| 4,753,987 A | 6/1988 | Dean | |
| 4,988,772 A | 1/1991 | Riffle | |
| 5,013,556 A | 5/1991 | Woodle | |
| 5,098,954 A | 3/1992 | Riffle | |
| 5,183,861 A | 2/1993 | Riffle et al. | |
| 5,213,804 A | 5/1993 | Martin | |
| 5,395,619 A | 3/1995 | Zalipsky | |
| 5,439,978 A | 8/1995 | Parkinson | |
| 5,602,209 A | 2/1997 | Warchol | |
| 5,631,018 A | 5/1997 | Zalipsky | |
| 5,633,309 A | 5/1997 | Warchol | |
| 5,837,768 A | 11/1998 | Warchol | |
| 5,854,331 A | 12/1998 | Ma | |
| 5,891,468 A | 4/1999 | Martin | |
| 5,980,690 A | 11/1999 | Warchol | |
| 6,056,973 A | 5/2000 | Allen | |
| 6,180,134 B1 | 1/2001 | Zalipsky | |
| 6,214,388 B1 | 4/2001 | Benz | |
| 6,234,381 B1 | 5/2001 | Hasegawa | |
| 6,316,204 B1 | 11/2001 | Shyjan | |
| 6,465,582 B1 | 10/2002 | Higginbottom | |
| 6,566,426 B1 | 5/2003 | Kanaida | |
| 7,160,553 B2 | 1/2007 | Gibbins | |
| 7,178,610 B2 | 2/2007 | Bell | |
| 2003/0161791 A1 | 8/2003 | Bentley et al. | |
| 2006/0032632 A1 | 2/2006 | Bell | |
| 2006/0051315 A1 | 3/2006 | Scaria | |
| 2006/0246126 A1 | 11/2006 | Allen | |
| 2007/0111895 A1 | 5/2007 | Bell | |

*Primary Examiner* — Paul Dickinson

(74) *Attorney, Agent, or Firm* — Thomas G. Peterson; Bradley Arant Boult Cummings LLP

(57) ABSTRACT

The present disclosure provides novel functional polyoxazoline derivatives prepared by terminating polyoxazoline polymerization with inert chemical groups. In addition, the present disclosure demonstrates the synthesis of novel electrophilic initiators with protected functional groups capable of initiating oxazoline polymerization and capable of surviving the conditions of polymerization. These initiators are used to synthesize the above inert-terminal polyoxazoline derivatives as well as other polyoxazolines with active terminal groups. Furthermore, the present disclosure provides for polyoxazoline-lipid conjugates and liposomal compositions prepared using such polyoxazoline-lipid conjugates. Methods of using the foregoing to prepare conjugates with target molecules are also disclosed.

19 Claims, No Drawings

US 9,284,411 B2

POLYOXAZOLINES WITH INERT TERMINATING GROUPS, POLYOXAZOLINES PREPARED FROM PROTECTED INITIATING GROUPS AND RELATED COMPOUNDS

CROSS-REFERENCE TO RELATED APPLICATIONS

This application is a continuation of application Ser. No. 13/003,306, filed on Jan. 9, 2011, now U.S. Pat. No. 8,883, 211, to be issued on Nov. 11, 2014. U.S. application Ser. No. 13/003,306 is a national stage under 35 U.S.C. §371 of International Application PCT/US09/50286, filed on Jul. 10, 2009, and which is currently pending. International Application PCT/US09/50286 is entitled under U.S.C. §119(e) to the benefit of the filing date of provisional U.S. Patent Application 61/079,799, filed on Jul. 10, 2008, which is currently expired.

FIELD OF THE DISCLOSURE

Generally, the present disclosure relates to certain polyoxazoline derivatives, methods of synthesis for such polyoxazoline derivatives, intermediate compounds useful in producing such polyoxazoline derivatives and conjugates of the polyoxazoline derivatives with target molecules, such as therapeutic, diagnostic and/or targeting agents. Specifically, the present disclosure relates to polyoxazoline derivatives terminated with inert chemical groups.

BACKGROUND

Polymer-modified therapeutics have proven to be of great utility in modern pharmaceutical science. Due to the success of polymer-modified therapeutics, it is of interest to expand the range of polymers suitable for such applications, especially to provide polymers having properties not possessed by polymers of the prior art. A need exists for functional, water-soluble, non-toxic polymers which can be used to prepare desired conjugates with target molecules. To prepare these therapeutic conjugates it is frequently necessary to synthesize water soluble polymers of high molecular weight and high purity. The present disclosure provides homo-functional polyoxazoline compounds, terminated with inert groups, which provide ready coupling to a range of target molecules, such as but not limited to, therapeutic, diagnostic and/or targeting moieties. In addition, the present disclosure provides some novel polyoxazolines, which may or may not be homo-functional, and which are prepared from novel polyoxazoline initiators disclosed here for the first time.

DETAILED DESCRIPTION

Definitions

As used herein, the term "POZ", "POZ compound" or "POZ polymer" refers to a polymer of 2-substituted-2-oxazoline containing a repeating unit having the structure —[N(COR$_2$)CH$_2$CH$_2$]$_n$— in which R$_2$ is independently selected for each repeating unit from an unsubstituted or substituted alkyl, alkenyl, aralkyl or heterocyclylalkyl group and n is from 3-1000; in one embodiment, the unsubstituted or substituted alkyl, alkenyl, aralkyl or heterocyclylalkyl groups comprise from 1-10 carbon atoms, and in a further specific embodiment, R$_2$ is methyl, ethyl, isopropyl or n-propyl.

As used herein, the term "PMOZ" refers to POZ with the repeating unit having the structure —[N(COCH$_3$)CH$_2$CH$_2$]$_n$—.

As used herein, the term "PEOZ" refers to POZ with the repeating unit having the structure —[N(COCH$_2$CH$_3$)CH$_2$CH$_2$]$_n$—.

As used herein, the term "PiPrOZ" refers to POZ with the repeating unit having the structure —[N(COCH(CH$_3$)$_2$)CH$_2$CH$_2$]$_n$—.

As used herein, the term "PnPrOZ" refers to POZ with the repeating unit having the structure —[N(CO(CH$_2$CH$_2$CH$_3$))CH$_2$CH$_2$]$_n$—.

As used herein, the terms M-POZ, M-PMOZ, M-PEOZ, M-PiPrOZ, and M-PnPrOZ refers to the polymers above in which the nitrogen on the initiating end is bound to methyl.

As used herein, the term "POZ derivative" or "polyoxazoline derivative" refers to a structure comprising a POZ polymer, the POZ polymer having an active functional group on at least one of the initiator end, the terminal end, or a pendent position of the POZ polymer, the active functional group capable of forming a linkage, directly or indirectly, with a chemical group on a target molecule.

As used herein, the term "target molecule" refers to any molecule having a therapeutic or diagnostic application or a targeting function, wherein the target molecule is capable of forming a linkage with an active functional group on a POZ polymer or a POZ derivative of the present disclosure, including, but not limited to, a therapeutic agent (such as but not limited to a drug), a diagnostic agent, a targeting agent, an organic small molecule, an oligonucleotide, a polypeptide, an antibody, an antibody fragment, a protein, a carbohydrate such as heparin or hyaluronic acid, or a lipid such as a phospholipid.

As used herein, the term "active functional group" refers to those groups that react readily with electrophilic or nucleophilic groups or that react readily by cylcoaddition reactions, in contrast to those groups that require strong catalysis, high temperatures or impractical reaction conditions in order to react.

As used herein, the term "inert group" "inert moiety" or "inert chemical group" means a group that will not readily form a linkage, directly or indirectly, with a chemical group on a target molecule or POZ derivative.

As used herein, the term "link", "linked" "linkage" or "linker" when used with respect to a POZ derivative described herein, or components thereof, refers to groups or bonds that normally are formed as the result of a chemical reaction and typically are covalent linkages.

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

As used herein, the term "alkyl", whether used alone or as part of a substituent group, includes straight chain hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)_2$, $-CH(CH_2CH_3)CH(CH_3)CH(CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, cholesteryl, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl" and "unsubstituted alkynyl" refers to alkyl, alkenyl and alkynyl groups that do not contain heteroatoms.

The phrase "substituted alkyl", "substituted alkenyl" and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, an oxygen atom in groups such as alkoxy groups and aryloxy groups; a sulfur atom in groups such as, alkyl and aryl sulfide groups, sulfone groups, sulfonyl groups, and sulfoxide groups; a silicon atom in groups such as in trialkylsilyl groups, dialkylarylsilyl groups, alkyldiarylsilyl groups, and triarylsilyl groups; and other heteroatoms in various other groups.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl and also includes aryl groups in which one or more aromatic carbons of the aryl group is bonded to a substituted and/or unsubstituted alkyl or alkenyl group as defined herein. This includes bonding arrangements in which two carbon atoms of an aryl group are bonded to two atoms of an alkyl or alkenyl group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted aralkyl" refers to unsubstituted alkyl or alkenyl groups as defined above in which a hydrogen or carbon bond of the unsubstituted or substituted alkyl or alkenyl group is replaced with a bond to a substituted or unsubstituted aryl group as defined above. For example, methyl ($CH_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to, furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes the heterocyclyl group in which one of the carbons is bonded to one of the non-carbon or carbon atoms such as, but not limited to, those atoms described above with respect to a substituted alkyl and substituted aryl groups and also includes heterocyclyl groups in which one or more carbons of the heterocyclyl group is bonded to a substituted and/or unsubstituted alkyl, alkenyl or aryl as defined herein. This includes bonding arrangements in which two carbon atoms of a heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocyclylalkyl" refers to unsubstituted alkyl or alkenyl groups as defined above in which a hydrogen or carbon bond of the unsubstituted alkyl or alkenyl group is replaced with a bond to a substituted or unsubstituted heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

General Description

Polyoxazolines (POZ) are polymers prepared from 2-substituted-2-oxazoline monomers. These polymers are water soluble and have been reported to be nontoxic in mammalian model systems. POZ is generally prepared by reaction of the appropriate stoichiometric amount of 2-alkyl-2-oxazoline with an electrophilic initiator, such as triflic acid ($CF_3$—$SO_3$—H), methyl p-toluenesulfonate (or "tosylate", $CH_3$—$OSO_2$—$C_6H_4$—$CH_3$) or methyl triflate ($CH_3$—$OSO_2$—$CF_3$), followed by termination with a nucleophile such as hydroxide or an amine. The polymer produced is conveniently described in shorthand with the initiating group designated by the leftmost group and the terminating group designated by the rightmost group, with the 2-alkyl-2-oxazoline component in the middle. Therefore, when this shorthand description is used in the current specification, it is intended that the left side of the designation presents the "initiator end" and the right side of the designation presents the "terminal end", unless designated otherwise. For example, when the 2-substituted-2-oxazoline is 2-methyl-2-oxazoline, methyl tosylate is used as the initiator and hydroxide is used as the terminator, the following polymer is produced:

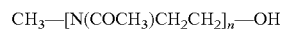

$CH_3$—[$N(COCH_3)CH_2CH_2$]$_n$—OH

The polymer above is conveniently described in shorthand notation as M-PMOZ-OH, in which the methyl initiator is designated by the leftmost M (at the initiator end), PMOZ represents polymethyloxazoline with the methyl of the repeating unit designated by the M of PMOZ, and the terminating hydroxyl is designated by the —OH (at the terminal end). The degree of polymerization, n, can range from approximately 3 to about 1000.

Another commonly used monomer is 2-ethyl-2-oxazoline, which with methyl triflate initiation and hydroxide termination provides the following POZ polymer:

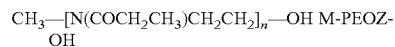

$CH_3$—[$N(COCH_2CH_3)CH_2CH_2$]$_n$—OH M-PEOZ-OH

The polymer above is conveniently described in shorthand notation as M-PEOZ-OH, in which the methyl initiator is designated by the leftmost M (at the initiator end), PEOZ represents polyethyloxazoline with the ethyl of the repeating unit designated by the E of PEOZ, and the terminating hydroxyl is designated by the —OH (at the terminal end). Other commonly used monomers are 2-n-propyl- and 2-iso-propyl-2-oxazoline.

More complex electrophiles and nucleophiles can be used. For example, initiation of 2-ethyl-2-oxazoline polymerization with benzyl bromide and termination with excess ethylene diamine yields the following polymer:

$C_6H_5$—$CH_2$—[$N(COCH_2CH_3)CH_2CH_2$]$_n$—NH—$CH_2CH_2$—$NH_2$

Also, different monomers can be used in the same polymer to yield various random and block copolymers.

The polymerization process is referred to as a living, cationic polymerization since initiation with an electrophile produces an oxazolinium cation that then reacts in a chain reaction with additional monomer units to produce a growing, "living" cation with an oxazolinium cation at the chain terminal end.

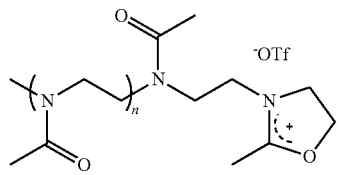

One can predict the products of termination by assuming that the living cation can be represented in the following non-cyclic form, although in reality the cyclic form is certainly the most important, and the desired products are produced by nucleophilic attack on the 5-position of the ring:

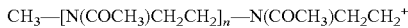

In the current disclosure this cation will be represented as M-PMOZ$^+$. As noted above, this POZ cation can be "terminated" by reacting with nucleophiles such as hydroxide or amines. Interestingly, termination with the weak nucleophile water does not give the desired product of attack at the 5-position of the ring (the "thermodynamic" product) but rather gives attack in the 2-position (the "kinetic" product). This kinetic product is not stable and can rearrange to give an ester product or undergo reversal to cation (O. Nuyken, G. Maier, A. Gross, Macromol. Chem. Phys. 197, 83-85 (1996)). Hydrolysis of the ester produces a secondary amine impurity. Another common impurity results from chain transfer in which one chain is terminated and a new chain is initiated with a proton (discussed in Patent Cooperation Treaty Application No. PCT/US200802626. As a consequence of chain transfer the polyoxazolines prepared to date with functional initiators contain appreciable amounts of product without the functional initiator. Greg: I am leaving this reference to you.

Hydroxyl-terminated polymers can be further modified to give active derivatives. For example, Zalipsky reacted the terminal —OH with glutaric anhydride to give a POZ terminated with a glutarate group (M. C. Woodle, C. M. Engbers and S. Zalipsky, Bioconjugate Chem., 1994, 5, 493-496).

M-PMOZ-O$_2$C—CH$_2$CH$_2$CH$_2$—CO$_2$H

The above polymer was activated as the succinimidyl ester and coupled to phospholipids and used to prepared POZ-modified liposomes. These liposomes were found to have similar properties to PEG-modified liposomes, Amine-terminated polymers also provide useful reactive groups for further derivatization. For example, termination with cyclic diamine piperazine gives a POZ terminated with the active group —NC$_4$H$_8$NH.

It is also possible to terminate the living POZ cation with complex nucleophiles to provide ester groups that can be deprotected to give carboxylic acids (described in Patent Cooperation Treaty Application No. PCT/US08/02626, which is hereby incorporated by reference herein for this teaching):

Oxazoline polymerizations can also be initiated with functional electrophiles. For example, the electrophilic initiator ethyl 3-bromopropionate has been used to initiate 2-ethyl-2-oxazoline polymerization. Termination with hydroxide gives the following difunctional polymer:

An alternative functional initiator is provided by use of functional oxazolinium cations. For example, Gaertner has reacted one mole of methyl triflate with one mole of various 2-substituted-2-oxazolines to obtain the corresponding oxazolinium-2-cation and used this electrophile to initiate polymerization and obtain a polyoxazoline with a functional group in the initiator position (F. C. Gaertner, R. Luxenhofer, B. Blechert, R. Jordan and M. Essler, J. Controlled Release, 2007, 119, 291-300). As noted above, chain transfer leads to formation of appreciable amounts of polymer initiated with a proton rather than the functional initiator.

It is noteworthy that POZs having the same functional group on the initiator end and the terminal end are chemically different; the group at the initiator end is attached to nitrogen while the group at the terminal end is attached to carbon. For example, the following two polymers are both propionic acid derivatives of PMOZ but differ in that the propionic acid at the initiator end is attached to nitrogen and the propionic acid at the terminal end is attached to carbon (the beginning or ending monomer unit is shown for clarity):

HOOCCH$_2$CH$_2$—N(COCH$_3$)CH$_2$CH$_2$-PMOZ-OH

M-PMOZ-N(COCH$_3$)CH$_2$CH$_2$—O—CH$_2$CH$_2$COOH

A third route to preparing polyoxazolines with active functional groups, in addition to initiation or termination with functional electrophiles or nucleophiles, is to copolymerize a monomer such as 2-ethyl-2-oxazoline with an oxazoline monomer having an active functional group in the 2-position. For example, Jordan and colleagues have prepared oxazolines with acetylenes and protected aldehydes, carboxylic acids and amines in the 2-position (F. C. Gaertner, R. Luxenhofer, B. Blechert, R. Jordan and M. Essler, J. Controlled Release, 2007, 119, 291-300). Copolymerization of these functional monomers with 2-ethyl-2-oxazoline gives random copolymers with multiple side-chain or "pendent" active functional groups. For example, initiation with methyl triflate of copolymerization of 2-ethyl-2-oxazoline and 2-pentynyl-2-oxazoline, followed by termination with piperazine (NHC$_4$H$_8$NH) gives the following random copolymer:

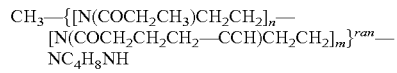

The superscript "ran" indicates that the polymer is a random copolymer. Block copolymers can also be prepared, Values of n are typically around 20-30 while m is typically around 2-5. In the above case the acetylene group is an active group and can participate in various cylcoaddition and other reactions.

These various functional polyoxazolines have been coupled to peptides, proteins and liposomes for a range of biomedical applications.

General methods for the synthesis of POZ polymers and POZ derivatives can be found in Patent Cooperation Treaty Application No. PCT/US08/02626, specifically, pages 14-21, which is hereby incorporated by reference herein

SUMMARY

The present disclosure provides novel functional polyoxazoline derivatives prepared by terminating polyoxazoline living cations with inert chemical groups. This route to polyoxazolines has not been previously utilized. In one embodiment, the inert chemical group is a nucleophilic group that are used to terminate the polymerization reaction. Exemplary inert chemical groups include substituted or unsubstituted alkyl or aryl mercaptides moieties. These alkyl or aryl mercaptide moieties can be used as terminating nucleophiles to terminate the polymerization reaction and provide the polyoxazoline derivative with an inert alkyl- or aryl-thioether terminating group. In contrast, all POZ derivatives described to date have possessed a chemically-reactive, functional terminating group, typically a hydroxyl (from hydroxide termination), an ester (from carboxyl termination) or an amine (from amine termination). Such polyoxazoline derivatives with inert chemical groups at the terminal position may contain one or more active functional groups at the initiator position or a pendent position.

In addition, the present disclosure demonstrates the synthesis of novel electrophilic initiators with protected functional groups capable of initiating oxazoline polymerization and capable of surviving the conditions of polymerization. These initiators are used to synthesize the above inert-terminal polyoxazoline derivatives as well as other polyoxazolines with active terminal groups.

Furthermore, the present disclosure provides novel functional polyoxazoline derivatives prepared by initiating oxazoline polymerization with the novel electrophilic initiators with protected functional groups. The produced polyoxazoline derivatives may have inert chemical groups or active functional groups at the terminal position. Furthermore, such polyoxazoline derivatives may contain one or more active functional groups at the initiator position and/or pendent positions.

In addition, the present disclosure provides novel polyoxazoline-lipid conjugates and liposomal compositions incorporating the polyoxazoline-lipid conjugates. In one embodiment, the polyoxazoline portion of the polyoxazoline-lipid conjugate comprises an active functional group at the pendent position. The polyoxazoline portion may contain additional active functional groups as well.

In the present disclosure, whenever a polyoxazoline derivative or polyoxazoline polymer is mentioned, the polyoxazoline polymer may be one characterized with low polydispersity (PD) values and increased purity; such polymers are useful in pharmaceutical applications. In a particular embodiment, the methods of the present disclosure provide for polyoxazoline derivatives with low PD values at increased MW values. In such embodiments, at least one polyoxazoline polymer chain has a polydispersity value of less than or equal to 1.2, less than or equal to 1.1 or less than or equal to 1.05. Methods of synthesizing polyoxazoline polymers and derivatives thereof with low PD values are discussed in Patent Cooperation Treaty Application Nos. PCT/US2008/002626 and PCT/US2008/078159, which are hereby incorporated by reference for such teaching.

Polyoxazoline Derivatives with Inert Chemical Groups at the Terminal Position

In one embodiment, the present disclosure provides a polyoxazoline derivative with an inert moiety at the terminal position. In one embodiment, the polyoxazoline derivative with an inert moiety at the terminal position is a monofunctional polyoxazoline derivative. In such an embodiment, a first active functional group may be present at the initiator position or one or more of the pendent positions. In an alternate embodiment, the polyoxazoline derivative with an inert moiety at the terminal position contains multiple copies of the same functional group at pendent positions and an inert moiety at the initiator position. In yet another alternate embodiment, the polyoxazoline derivative with an inert moiety at the terminal position contains an active functional group at the initiator position and an inert moiety at pendent positions. In still a further alternate embodiment, the polyoxazoline derivative with an inert moiety at the terminal position contains multiple copies of the same functional group at pendent positions and the same active functional group at the initiator position.

The polyoxazoline derivative with an inert moiety at the terminal position may be prepared by initiating oxazoline polymerization with an electrophile, such as, but not limited to, triflic acid (H—$SO_3$—$CF_3$) or a triflate-(—$OSO_2$—$CF_3$) or a tosylate-(—$OSO_2$—$C_6H_4$—$CH_3$) containing moiety, to generate oxazolinium ions which initiate the living cation polymerization as discussed above. The electrophile may contain an active functional group as discussed above. In an alternate method, oxazoline polymerization can be initiated by mixing an electrophile initiating agent, such as, but not limited to, triflic acid ($CF_3$—$SO_3$—H), an alkyl triflate (R—$OSO_2$—$CF_3$) or an alkyl tosylate (R—$OSO_2$—$C_6H_4$—$CH_3$), with an oxazoline monomer (such as a 2-substituted-2-oxazoline monomer) in equimolar amounts. When the 2-substituent contains a functional group or protected functional group, the result of the reaction is an oxazolinium cation with an active functional group in the pendent position. This oxazolinium cation can then be used to initiate oxazoline polymerization. This method of initiation gives a polyoxazoline with the active functional group attached to the initiator position. If the electrophilic initiating group contains an active functional group, the active functional group may be protected (such as, but not limited to, a carboxylic acid protected as an ester).

Active functional groups may also be present at the pendent positions of the polyoxazoline polymer chain. Active functional groups on the pendent side chains may also be protected as well. Examples of active functional groups at the pendent position of both random and block copolymers are provided in Patent Cooperation Treaty Application No. PCT/US2009/030762, which is hereby incorporated herein by reference for such teaching.

This use of polyoxazoline derivatives with inert groups at the terminal position provides several advantages over the prior art. As discussed above, the polyoxazoline derivatives with inert terminal groups may be prepared as monofunctional POZ derivatives or multi-functional POZ derivatives. Furthermore, when the POZ derivative is a monofunctional POZ derivative with an active functional group at the initiator position, the synthesis can be carried out using only a stoichiometric amount of electrophile initiator containing the active functional group. The alternative approach to synthesizing monofunctional POZ derivatives using a nucleophilic terminating group containing an active functional group requires a significant excess of the terminating agent (usually 2 to 3 fold excess). Use of excess reagents is costly (especially for complex terminating groups) and complicates purification, which may lead to decreased yield, higher percentage of impurities and increased cost. An additional advantage of the present disclosure is that incorporation of the active functional group is automatically quantitative once polymerization is achieved unless there is chain transfer. Functionalization using a nucleophilic terminating group containing an active functional group fails for some nucleophiles and can yield side products (O. Nuyken, G. Maier, A. Gross, Macromol, Chem. Phys. 197, 83-85 (1996)). Termination with the inert nucleophilic group as described herein, such as but not limited to, alkyl and aryl mercaptides, is a highly efficient reaction and does not readily generate unwanted side products, Monofunctional POZ derivatives are useful for coupling to complex, multifunctional target molecules such as proteins. By the use of monofunctional derivatives one avoids crosslinking and aggregation. Multi-functional POZ derivatives are also useful (see Patent Cooperation Treaty Application No. PCT/US2009/030762, which is hereby incorporated herein by reference for such teaching).

A major advantage of synthesizing monofunctional POZ derivatives with the functional group in the initiating position is that chain transfer impurities can be readily removed. For example, the applicants have prepared $CH_3$—[N($COCH_2CH_3$)$CH_2CH_2$]$_n$—S—$CH_2CH_2$—$CO_2H$ by initiation of polymerization with methyl triflate followed by termination with mercaptopropionic acid ethyl ester (followed by hydrolysis). This product will be contaminated with chain transfer product in which the initiating methyl group is replaced with a hydrogen atom. This chain transfer product cannot be removed. On the other hand, if the acid group is present in the initiating group, as we have described in the present disclosure, the chain transfer product can be removed. For example, in the case of initiating with acid and terminating with benzyl mercaptide the desired product is the acid shown below, and the chain transfer product is the polymer with hydrogen in the initiating position. The desired product, free of chain transfer product, can be isolated by ion exchange chromatography. Such chromatography also removes secondary amine formed by termination with water impurity. We have found that these impurities can constitute a significant percentage of the reaction products.

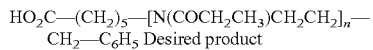
$HO_2C$—($CH_2$)$_5$—[N($COCH_2CH_3$)$CH_2CH_2$]$_n$—
$CH_2$—$C_6H_5$ Desired product

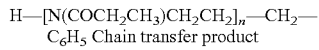
H—[N($COCH_2CH_3$)$CH_2CH_2$]$_n$—$CH_2$—
$C_6H_5$ Chain transfer product This approach to removing chain transfer product is also useful in preparing multifunctional materials, as shown below, since chain transfer leads to loss of the functional group at the initiator position.

As described above, initiation of oxazoline polymerization is generally done using an electrophile, such as, but not limited to, a triflate-(—$OSO_2$—$CF_3$—) or a tosylate-(—$OSO_2$—$C_6H_4$—$CH_3$) containing moiety. Other electrophiles may also be utilized, although generally halides must be avoided since they do not give the desired living-cation polymerization mechanism (Patent Cooperation Treaty Application No. PCT/US2008/002626, which is hereby incorporated herein by reference for such teaching). Since many groups may react with the electrophilic initiator, in certain embodiments, the electrophilic initiator is protected. For example, when a triflate is the electrophilic initiator, the triflate may be provided as a protected ester-triflate. In this protected form, the electrophilic initiator is capable of initiating polymerization and any reactive groups on the electrophilic initiator are maintained in a non-reactive form.

A general representation of one embodiment of the polyoxazoline derivatives with inert chemical groups at the terminal position and methods of synthesizing the same is provided in scheme 1 below.

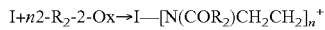
I+n2-$R_2$-2-Ox→I—[N(COR$_2$)CH$_2$CH$_2$]$_n$$^+$

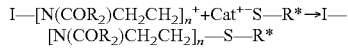
I—[N(COR$_2$)CH$_2$CH$_2$]$_n$$^+$+Cat$^+$$^-$S—R*→I—
[N(COR$_2$)CH$_2$CH$_2$]$_n$—S—R*     Scheme 1 wherein:

I represents the initiating group (a group present at the initiator position);

2-$R_2$-2-Ox represents a 2-substituted 2-oxazoline monomer;

n=3 to 1000, $R_2$ is independently selected for each repeating unit from an unsubstituted or substituted alkyl, alkenyl, aralkyl or heterocyclylalkyl group; in one embodiment, the unsubstituted or substituted alkyl, alkenyl, aralkyl or heterocyclylalkyl groups comprise from 1-10 carbon atoms, in a further specific embodiment, $R_2$ is methyl, ethyl, isopropyl or n-propyl; $R_2$ is defined as occupying the pendent position;

Cat$^+$ represents a cation, including but not limited to a metal cation such as, but not limited to, Li$^+$, Na$^+$ and K$^+$;

S is a sulfur atom; and

R* is chosen from the same group as $R_2$ but is independent of $R_2$.

In this embodiment, I may be an active functional group or an inert moiety. Furthermore, the group at $R_2$ may be an active functional group or an inert moiety. However, the final polyoxazoline derivative should have one active functional group present. The active functional group may be any chemical group capable of forming a linkage with a binding partner on a target molecule as described herein. In one embodiment, the active functional group may be an alkyne, an oxyamine, an aldehyde, a ketone, an ester, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or orthopyridyl disulfide.

In one embodiment, I is a triflate-(—$OSO_2$—$CF_3$) or a tosylate-(—$OSO_2$—$C_6H_4$—$CH_3$) containing moiety. It should be noted that one or more active functional groups may be present in the final polymer, with said active functional groups being at either the initiator position (represented by I above), or one or more of the pendent positions (represented by $R_2$ above).

The I group may also be in a protected form as discussed herein. In one embodiment, the protected I group is a protected triflate as described herein. In this embodiment, the polyoxazoline derivative with inert chemical groups at the terminal position and methods of synthesizing the same is provided in scheme 2 below.

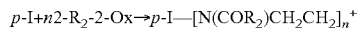
p-I+n2-$R_2$-2-Ox→p-I—[N(COR$_2$)CH$_2$CH$_2$]$_n$$^+$

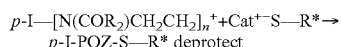
p-I—[N(COR$_2$)CH$_2$CH$_2$]$_n$$^+$+Cat$^+$$^-$S—R*→
p-I-POZ-S—R* deprotect

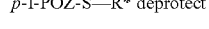
p-I-POZ-S—R*→I-POZ-S—R*     Scheme 2

In these reactions, the substituents are as defined in scheme 1 above, with the exception that p represents a protecting group.

A further example of polyoxazoline derivatives with inert chemical groups at the terminal position and methods of synthesizing the same is provided in scheme 3 below. In this example, the initiating group I is represented by a protected electrophilic initiating group (in this case a triflate containing moiety).

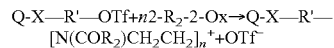
Q-X—R'—OTf+n2-$R_2$-2-Ox→Q-X—R'—
[N(COR$_2$)CH$_2$CH$_2$]$_n$$^+$+OTf$^-$

Q-X—R'—[N(COR$_2$)CH$_2$CH$_2$]$_n$$^+$+R*—S$^-$Cat$^+$→
Q-X—R'—[N(COR$_2$)CH$_2$CH$_2$]$_n$—S—
R* deprotect

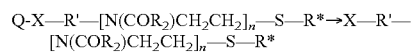
Q-X—R'—[N(COR$_2$)CH$_2$CH$_2$]$_n$—S—R*→X—R'—
[N(COR$_2$)CH$_2$CH$_2$]$_n$—S—R*     Scheme 3

In these reactions, Q-X—R'—OTf represents the electrophilic initiator, in this case a triflate-containing initiating moiety containing a protected active functional group, wherein Q-X- represents the protected active functional group, X represents the functional group, R' represents a linking group, and 2-$R_2$-2-Ox, n, $R_2$, R* and Cat$^+$ are as defined above in scheme 1.

The functional group X can be, but is not limited to, one of the following: an alkyne, an oxyamine, an aldehyde, a ketone, an ester, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or orthopyridyl disulfide.

The reaction shown below in scheme 4 provides a specific embodiment of the formula represented by scheme 3. In this reaction, 2-Et-2-Ox represents 2-ethyl-2-oxazoline, the ester-triflate $CH_3—O_2C—(CH_2)_5—OTf$ is Q-X—R'—OTf (the protected electrophilic initiating moiety), the methyl ester group, $CH_3—O_2C—$, is Q-X- (the protected active functional group), $HO_2C—$ is X (the deprotected functional group), Na+ is the $Cat^+$, $R_2$ is ethyl, $R^*$ is $—CH_2—C_6H_5$, and R'— is $—(CH_2)_5—$.

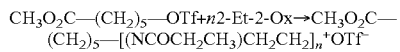

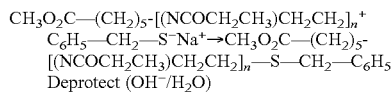

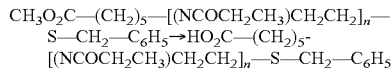

Scheme 4

A further example of polyoxazoline derivatives with inert chemical groups at the terminal position and methods of synthesizing the same is provided in scheme 5 below. As discussed herein, active functional groups may be present in at least one pendent position in the oxazoline polymer chain. In this example (scheme 5), I' is an inert group and a nucleophilic inert group is used to terminate a polymerization of oxazoline polymers with an active functional group in at least one pendent position of the polyoxazoline polymer.

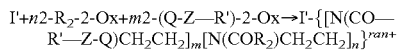

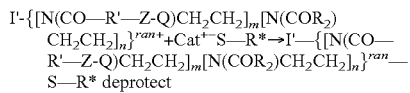

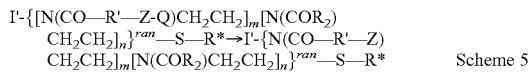

Scheme 5

In this series of reactions, I' is an inert group selected from the groups described in $R_2$ in Scheme 1; in one embodiment, I' is hydrogen or an alkyl. 2-(Q-Z—R')-2-Ox represents a 2-substituted 2-oxazoline monomer with a protected active functional group Q-Z—R'— in the $R_2$-position, wherein Q is the protecting group, Z is the protected active functional group and R' is a linking group. In one embodiment, Z is an active functional group described in Patent Cooperation Treaty Application No. PCT/US08/02626, which is hereby incorporated by reference herein; alternatively, Z can be one of the groups described above for scheme 3. m is an integer from 1-1000 and n is an integer from 0-1000. 2-$R_2$-2-Ox, $R_2$, $Cat^+$ and $R^*$ are as defined above in scheme 1. Furthermore, in certain embodiments, the oxazoline monomer containing the active functional group at the $R_2$-position may be the only monomer used (where n=0)

Block copolymers of the polyoxazoline derivatives with inert chemical groups at the terminal position can also be synthesized according to the above and can be represented as shown below in scheme 6

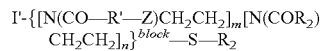

Scheme 6

A specific example of the synthesis shown in scheme 5 is exemplified by the product shown in scheme 7. In this example, I' is methyl triflate, 2-(Q-Z—R')-2-Ox is the oxazoline monomer shown below, where Q-Z— is methyl ester and R' is $—CH_2CH_2—$, the $R_2$ group in 2-$R_2$-2-Ox is $—CH_2CH_3$, and $Cat^+S—R^*$ is $C_6H_5—CH_2—S^-Na^+$.

Scheme 7

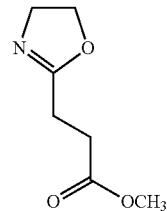

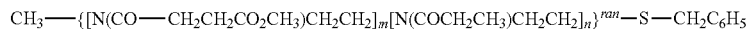

After deprotection of the Z group by ester hydrolysis, the following POZ derivative is produced.

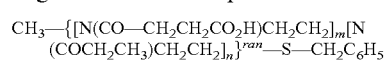

The same POZ derivative can also be synthesized in a block copolymer as discussed above and shown in scheme 8.

Scheme 8

In the above embodiments containing distinct polyoxazoline groups (Schemes 5-8), the polyoxazoline polymer may be a homopolymer; likewise the polyoxazoline polymer may be a random or block copolymer containing one or more units of a first polyoxazoline separated by one or more units of a second polyoxazoline. For example, the polyoxazoline polymer may be a homopolymer when n=0. Furthermore, the polyoxazoline polymer may be a random or block copolymer when n>1. In such an embodiment, the single units or blocks of a first polyoxazoline may be separated by single units or blocks of a second polyoxazoline.

In one embodiment, the polyoxazoline polymer that contains $R_2$ may be a homopolymer or a random or block copolymer containing one or more units of a first polyoxazoline separated by one or more units of a second polyoxazoline by the selection of the appropriate $R_2$ group. $R_2$ is independently selected for each repeating unit of the polyoxazoline polymer. In one embodiment, $R_2$ groups for the first and second polyoxazoline are independently methyl, ethyl, isopropyl or n-propyl. In an alternate embodiment, $R_2$ groups for the first and second polyoxazoline are independently a C1 to C4 alkyl group.

In one embodiment, the polyoxazoline polymer that contains $R_2$ is a homopolymer of a C1-C2 alkyl (such as methyl or ethyl) or a random or block copolymer of a C1-C2 alkyl. In such an embodiment, the C1-C2 alkyl homopolymer or random or block copolymer may comprise 50%, 75%, 90%, 95% of 99% of the total polyoxazoline polymer present.

The preparation of random and block copolymers is described in Patent Cooperation Treaty Application No. PCT/US2009/030762, which is hereby incorporated herein by reference for such teaching.

In any of the embodiments above, the protecting group is optional and may be included or eliminated as desired.

Synthesis of Protected Triflates

In certain embodiments of the present disclosure, the electrophile initiating group is protected. As discussed herein, protected sulfonate esters, including but not limited to triflates, may be used as the electrophilic initiating group. Preparation and utilization of triflate initiators which contain protected active functional groups is challenging in that the protected active functional group must be stable to both triflate preparation and triflate-initiated oxazoline polymerization. Additionally, the protecting group must be easily removed without destroying or causing unwanted reactions in the resulting POZ derivative. The case of mono-protected diols is illustrative. A commonly used alcohol protecting group is the benzyl ether. However, this protecting group is generally removed by hydrogenation or strong acid, and under these reaction conditions, the amide active functional groups of the POZ derivative will be damaged.

In our experiments, the tert-butyldiphenylsilyl (TBDPS) group is the only hydroxyl protecting group identified that is stable during triflate preparation and cationic polymerization. The alcohol-protecting group TBDPS was found to meet all the above requirements. An unprotected hydroxyl of a diol which has been monoprotected by the TBDPS group can be converted to the triflate without harming the TBDPS group. Also the TBDPS group tolerates oxazoline polymerization and can be removed readily by treatment with mild acid without harming or causing unwanted reactions in the resulting POZ derivative. An exemplary TBDPS-protected triflate group is shown below in Scheme 9.

Scheme 9

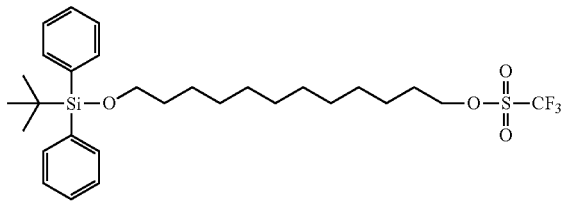

Similarly, we have found that ethyl 6-hydroxyhexanoate can be used as a protecting group and is stable during triflate preparation and cationic polymerization. Like TBDPS, the hydroxyl group at the 6 position of ethyl-6-hydroxyhexanoate can be converted to the triflate and this triflate can be used to initiate oxazoline polymerization. Finally, the ester group can be hydrolyzed by mild base yielding a carboxylic acid group without harming or causing unwanted reactions in the resulting POZ derivative.

The above compounds may be used to initiate oxazoline polymerization in any reaction described herein.

Additional Related Polymers

The novel electrophile initiators (such as the protected triflate groups and other groups described herein) may be used to prepare novel polyoxazoline derivatives in addition to the classes above. In one embodiment, such compounds may be represented by the general formula shown in scheme 10 below.

$\text{D-R}_3\text{-POZ-R}_4\text{—X}$    Scheme 10 wherein:
D is —OH, —CO$_2$H or a group containing an active —OH group or an active —CO$_2$H group;
$R_3$ and $R_4$ are linking groups;
POZ is a polyoxazoline polymer of the structure [N(COR$_2$)CH$_2$CH$_2$]$_n$
$R_2$ is independently selected for each repeating unit of the polyoxazoline polymer from an unsubstituted or substituted alkyl, alkenyl, aralkyl or heterocycylalkyl group;
X is an active functional group or a group capable of being converted to an active functional group, the active functional group capable of forming a linkage with a binding partner on a target molecule; and
n is an integer from 3-1000.

Exemplary X groups include, but are not limited to, an alkyne, an oxyamine, an aldehyde, a ketone, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or an orthopyridyl disulfide.

Exemplary $R_3$ groups include, but are not limited to, —(CH$_2$)$_p$— where p is an integer from 1-25. Exemplary $R_4$ groups include, but are not limited to, —S—CH$_2$—CH$_2$—.

As an example of a compound falling under scheme 10, use of the protected ester-triflate described in the preceding section to initiate polymerization of 2-methyl-2-oxazoline followed by termination with hydroxide gives the following polymer:

$\text{CH}_3\text{O}_2\text{C—(CH}_2\text{)}_5\text{—[N(COCH}_3\text{)CH}_2\text{CH}_2\text{]}_n\text{—OH}$ Deprotection yields the following:

$\text{HO}_2\text{C—(CH}_2\text{)}_5\text{—[N(COCH}_3\text{)CH}_2\text{CH}_2\text{]}_n\text{—OH}$ Similarly, initiation with the TBDPS-hydroxyl-protected triflate shown above in Scheme 9 can be used to prepare POZ derivatives with active functional groups at the terminal or pendent positions. The hydroxyl-protected triflate initiator can be used as the electrophile initiator to generate a POZ polymerization with a hydroxyl group at the initiator position and other terminating groups.

For example, use of the hydroxyl-protected triflate TBDPS described in the preceding section to initiate polymerization of 2-methyl-2-oxazoline followed by termination with hydroxide and deprotection gives the following useful polymer:

$\text{HO—(CH}_2\text{)}_{12}\text{—[N(COCH}_3\text{)CH}_2\text{CH}_2\text{]}_n\text{—OH}$ A particular application of the protected ester-triflate as initiator is to use ion-exchange chromatography of the resulting acid to prepare heterofunctional POZ derivatives free of chain transfer impurity.

The methods described above can also be used with the ester-triflate initiators to prepare heterofunctional compounds with initiator carboxyl and pendent functional groups. In one embodiment, such compounds may be represented by the general formula shown in scheme 11 below.

$\text{E-R}_3\text{-}\{\text{POZ}_I\text{-POZ}_{II}\}^a\text{—S—R*}$    Scheme 11 wherein:

R$_3$ and R$_2$ are as defined in Scheme 10 above;

E is —OH, —CO$_2$H or a group containing an active —OH group or an active —CO$_2$H group;

POZ$_I$ is a polyoxazoline polymer of the structure [N(CO—R'—Z)CH$_2$CH$_2$]$_m$ POZ$_{II}$ is a polyoxazoline polymer of the structure [N(COR$_2$)CH$_2$CH$_2$]$_n$ R' is an optional linking group Z is an active functional group or a group capable of being converted to an active functional group, the active functional group capable of forming a linkage with a binding partner on a target molecule;

R* is an unsubstituted or substituted alkyl, alkenyl, aralkyl, heterocycylalkyl group or an active functional group or a group capable of being converted to an active functional group, the active functional group capable of forming a linkage with a binding partner on a target molecule;

n is an integer from 0-1000, provided that when n=0, then m is >1;

m is an integer 1-1000; and a is ran, which indicates a random copolymer, or block, which indicates a block copolymer.

Exemplary active functional groups (Z and R*) include, but are not limited to, an alkyne, an oxyamine, an aldehyde, a ketone, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or an orthopyridyl disulfide.

Exemplary R$_3$ groups include, but are not limited to, —(CH$_2$)$_p$— where p is an integer from 1-25.

In this embodiment, Z and/or R* may be active functional groups, or Z may be an active functional group and R* may be an inert group.

As an example of a compound falling under scheme 11, use of the protected ester-triflate described in the preceding section to initiate polymerization polyoxazoline polymerization provides the following polymer:

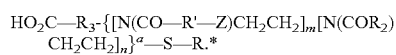

HO$_2$C—R$_3$-{[N(CO—R'—Z)CH$_2$CH$_2$]$_m$[N(COR$_2$)CH$_2$CH$_2$]$_n$}$^a$—S—R*

As an additional example of a compound falling under scheme 11, initiation with the TBDPS-hydroxyl-protected triflate shown above in Scheme 9 can be used to prepare heterofunctional compounds with initiator hydroxy and pendent functional groups.

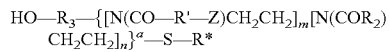

HO—R$_3$—{[N(CO—R'—Z)CH$_2$CH$_2$]$_m$[N(COR$_2$)CH$_2$CH$_2$]$_n$}$^a$—S—R*

As discussed herein, the polyoxazoline polymer may be homopolymer (when n=0) or a random or block copolymer.

Target Molecule-POZ Conjugates

The present disclosure describes a variety of POZ derivatives capable of forming a linkage with a target molecule to produce a target molecule-POZ conjugate as discussed above. In a general embodiment, the present disclosure provides for a target molecule-POZ conjugate having the general formula shown in scheme 9:

A$_a$-B-TM$_t$     9

Wherein,

A is a POZ derivative described herein, minus any leaving groups eliminated during the reaction of the active group on the POZ derivative with a binding partner on the target molecule;

a indicates the number of POZ derivatives bound, which will vary depending on the number of active functional groups on the POZ derivative and appropriate binding partners on the target molecule;

TM is a target molecule;

Subscript t is an integer indicating the number of TM bound, which will vary depending on the number of active functional groups on the POZ derivative and appropriate binding partners on the POZ derivative; and B is a linkage formed between the functional active groups of a POZ derivative of the present disclosure and a binding partner on the target molecule, it being understood that the nature of the B linkage will depend on the nature of the active functional group on the monofunctional POZ derivative and the binding partner on the target molecule. In one embodiment, the B linkage is a hydrolytically stable linkage. Exemplary active groups, binding partners and B linkages are described in Patent Cooperation Treaty Application No. PCT/US2008/002626 (see especially Table 3 therein), which is hereby incorporated by reference herein for such teaching (such listing is not meant to be exhaustive and other combinations and resulting B linkages may be envisioned given the teachings of the present disclosure).

As used herein, the term "target molecule" refers to any molecule having a therapeutic or diagnostic application or a targeting function, wherein the target molecule is capable of reacting with an active functional group on a POZ polymer or a POZ derivative of the present disclosure, including, but not limited to, a therapeutic agent, a diagnostic agent, a targeting agent, an organic small molecule, an oligonucleotide, an oligopeptide, a polypeptide, an antibody, an antibody fragment, a protein, a carbohydrate such as heparin or hyaluronic acid, or a lipid such as a phospholipid.

Examples of target molecule-POZ conjugates can be found in Patent Cooperation Treaty Application No. PCT/US2008/002626 (see especially Examples 17-18, 25-27 and 34-35) and Patent Cooperation Treaty Application No. PCT/US2009/030762 (see especially Examples 13-14), which are hereby incorporated by reference herein for such teachings.

POZ-Lipid Conjugates

The present disclosure also provides for polyoxazoline-lipid conjugates.

Polyoxazoline-lipid conjugates of the present disclosure comprise a lipid portion linked to a polyoxazoline portion. In one embodiment, the lipid portion comprises at least one hydrophobic moiety and a chemical group capable of forming a linkage with a chemical group on the polyoxazoline portion. In an alternate embodiment, the lipid portion comprises two hydrophobic moieties and the chemical group is located at the head group position and the polyoxazoline portion is linked to the lipid portion through the chemical group located at head group position.

In a general form the polyoxazoline-lipid conjugates of the present disclosure may be represented by the formula: LP-L-POZ, where LP represents the lipid portion, L represents a linkage between the lipid portion and the polyoxazoline portion and POZ represents the polyoxazoline portion. The lipid portion and the polyoxazoline portion are described below.

Lipids are a class of molecules that contain a hydrophobic portion and a hydrophilic portion. The hydrophobic and hydrophilic portions provide an amphipathic property to these molecules allowing them to aggregate in a specific manner to form bilayers and vesicles/liposomes in aqueous environments. Phospholipids are a type of lipids that have such amphipathic character. The head group of a phospholipid is hydrophilic whereas the tail groups are hydrophobic. The hydrophilic head group contains the negatively charged phosphate group, and may contain other polar groups. The hydrophobic tail group generally comprises long fatty acid hydrocarbon chains. When placed in an aqueous environment, phospholipids form a variety of structures depending on the specific properties of the phospholipid.

The lipid portion of the polyoxazoline-lipid conjugates may comprise any lipid capable of forming a vesicle/liposome, either alone or in combination with other lipid components of the liposomal compositions (described below). The lipids may be synthetic or naturally occurring. Regardless of the exact nature of the lipid comprising the lipid portion, the lipid contains a chemical group that is suitable for forming a linkage with a chemical group on the polyoxazoline portion. The nature of the linkage will depend on the chemical group present on the polyoxazoline portion and the chemical group present on the lipid portion. In one embodiment, the chemical group that forms the linkage with the polyoxazoline portion is located in the head group of the lipid portion. For example, the chemical group may be an amine group, hydroxyl group, aldehyde group or a carboxylic acid group; other chemical groups are not excluded. The polyoxazoline portion may be conjugated via appropriate chemical group on the initiator or the terminal end of the polymer.

In one embodiment, the lipid portion of the polyoxazoline-lipid conjugate comprises two hydrophobic moieties. The hydrophobic moieties are typically acyl chains containing an alkyl portion. The alkyl portion of the acyl chain may vary in length; in addition the alkyl portion may be saturated (contain no double bonds) or contain one or more areas of unsaturation (contain one or more double bonds). When unsaturated, the alkyl portion may have varying degrees of unsaturation, for example, from 1 to 4 areas of unsaturation. When the alkyl portion contains an area of unsaturation, the hydrogen atoms at the double bond may be in the cis or trans configuration. In one embodiment, the alkyl portion of the acyl chains contains from 14 to 24 carbons. The alkyl portions of the two hydrophobic moieties may be the same or may be different.

In one embodiment, the lipid is a phospholipid, a glycerolipid, or a sterol lipid. In a particular embodiment, the lipid is a phospholipid, such as, but not limited to, a phosphoglyceride or sphingolipid. Exemplary phosphoglycerides include, but are not limited to, phosphatidylcholine, phosphatidylinositol, phosphatidylethanolamine, phosphatidylglycerol, phosphatidylserine and phosphatidic acid; exemplary sphingolipids include, but are not limited to, sphingomyelin. In a specific embodiment, the lipid portion is phosphatidylethanolamine. Phosphatidyl ethanolamine contains a reactive amino group which can be used to form a linkage with the polyoxazoline portion.

The lipid portion of the polyoxazoline-lipid conjugate may be selected to impart desired characteristics to the liposomal compositions described herein. For example, the degree of unsaturation may be selected to provide desired properties to the liposomal compositions described herein. For example, increasing the degree of unsaturation of the lipid portion may impart fluidity to the liposomal composition; in addition, a cis configuration around the area of unsaturation may also impart increased fluidity to the liposomal composition. Likewise a saturated lipid portion may impart rigidity to the liposomal composition. The fluidity and/or rigidity may be selected to control, at least in part, the stability of the liposomal composition and/or the rate of release of a drug or a polyoxazoline-lipid conjugate from the liposomal composition. Generally, the more fluidic lipids are simpler to formulate and size than more rigid lipid components.

The polyoxazoline portion of the polyoxazoline-lipid conjugate may be created as described herein. In one embodiment, the polyoxazoline portion contains a pendant functional group that is capable of reacting with a binding partner on a target molecule. In this embodiment, the polyoxazoline portion may be represented by the formula: $-L_I-\{POZ_I-POZ_{II}\}^a-S-L_{II}-R^*$ or $I-\{POZ_I-POZ_{II}\}^a-S-L_{II}-$;

Wherein $POZ_I$ is a polyoxazoline polymer of the structure $-[N(CO-R'-Z)CH_2CH_2]_m$;

$POZ_{II}$ is a polyoxazoline polymer of the structure $[N(COR_2)CH_2CH_2]_n$;

R', $L_I$ and $L_{II}$ are each an optional linking group;

Z is an active pendent functional group or a group capable of being converted to an active functional group, the active functional group capable of forming a linkage with a binding partner on a target molecule;

$R_2$ is independently selected for each repeating unit of the polyoxazoline polymer from an unsubstituted or substituted alkyl, alkenyl, aralkyl or heterocycylalkyl group;

R* is an unsubstituted or substituted alkyl, alkenyl, aralkyl, heterocycylalkyl group or an active functional group or a group capable of being converted to an active functional group, the active functional group capable of forming a linkage with a binding partner on a target molecule;

I is a group present at the initiator position;

n is an integer from 0-1000, provided that when n=0, then m is >1;

m is an integer 1-1000; and a is ran, which indicates a random copolymer, or block, which indicates a block copolymer, provided that when n=0, a is block.

The pendent active functional groups are represented by the Z group in $POZ_I$; representative Z groups are provided in the present specification and any Z group disclosed herein may be used in the polyoxazoline-lipid conjugates described. In one embodiment, Z is an alkyne, an oxyamine, an aldehyde, a ketone, an ester, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or orthopyridyl disulfide. When an active functional group, R* may be these same groups. I may be any initiating group disclosed herein; in one embodiment, I is an inert group, such as H or an alkyl.

In one embodiment, $L_I$ and $L_{II}$ are each independently $-(CH_2)_f-NHCO-(CH_2)_g-$, $-(CH_2)_f-NHCO_2-(CH_2)_g-$ or $(CH_2)_h-$ wherein f, g and h are each an integer independently selected from 0-10.

In one embodiment, the polyoxazoline portion of the conjugate is soluble in aqueous environments. The nature of the pendent groups can change solubility to some extent. The solubility of the polyoxazoline portion permits the polyoxazoline portion to extend beyond the liposomal surface and into the extra-liposomal environment. In such a manner the polyoxazoline portion can effectively shield the liposomal surface and provide target molecules exposure to the extra-liposomal environment.

The polyoxazoline portion may be a homopolymer; likewise the polyoxazoline portion may be a random or block copolymer containing one or more units of a first polyoxazoline separated by one or more units of a second polyoxazoline. For example, the polyoxazoline portion may be a homopolymer when n=0 and the polyoxazoline portion contains only $POZ_I$. Furthermore, the polyoxazoline portion may be a random or block copolymer when n>1. In such an embodiment, the single units or blocks of $POZ_I$ may be separated by single units or blocks of polyoxazoline polymer represented by $POZ_{II}$.

In one embodiment, $POZ_{II}$ may be a homopolymer or a random or block copolymer containing one or more units of a first polyoxazoline separated by one or more units of a second polyoxazoline by the selection of the appropriate $R_2$ group. $R_2$ is independently selected for each repeating unit of the polyoxazoline polymer represented by $POZ_{II}$. In one embodiment, $R_2$ groups for the first and second polyoxazoline are independently methyl, ethyl, isopropyl or n-propyl. In an alternate embodiment, $R_2$ groups for the first and second polyoxazoline are independently a C1 to C4 alkyl group.

In one embodiment, the $POZ_{II}$ is a homopolymer of a C1-C2 alkyl (such as methyl or ethyl) or a random of block copolymer of a C1-C2 alkyl. In such an embodiment, the C1-C2 alkyl homopolymer or random or block copolymer may comprise 50%, 75%, 90%, 95% of 99% of the total polyoxazoline polymer present in the polyoxazoline portion.

The polyoxazoline polymer may contain a single active functional group or multiple active functional groups, the multiple active functional groups being the same or different. For example, in one embodiment at least one of the R* group and the $R_2$ group are an inert group. In an alternate embodiment, at least one of the R* group and the $R_2$ group are an active functional group.

In one embodiment, the polyoxazoline-lipid conjugate comprises a phospholipid as the lipid portion. In this embodiment, the polyoxazoline-lipid conjugate may be represented by the general structure:

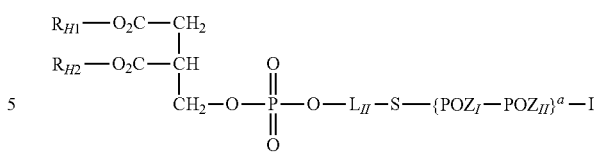

wherein $R_{H1}$ and $R_{H2}$ are each independently saturated alkyl groups or unsaturated alkyl groups and L is a linking group linking the hydrophilic moiety of the lipid portion and the polyoxazoline portion.

In an alternate embodiment, the polyoxazoline-lipid conjugate may be represented by the general structure:

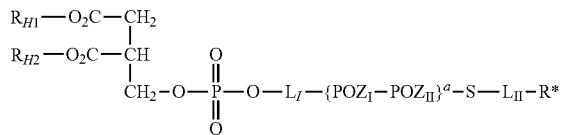

wherein $R_{H1}$ and $R_{H2}$ are as defined above.

As discussed above, the alkyl portion may be saturated or have one or more areas of unsaturation and can vary in chain length. As discussed above, the nature of the linkage will depend on the chemical group present on the polyoxazoline portion and the chemical group present on the lipid portion. In one embodiment, the chemical group that forms the linkage with the polyoxazoline portion is located in the head group of the lipid portion and the initiator end of the polyoxazoline portion. For example, the chemical group may be an amine group, hydroxyl group, aldehyde group or a carboxylic acid group; other chemical groups are not excluded.

In general the covalent attachment of polymers to a vesicle-forming lipid is accomplished by reaction of an active chemical group on the polyoxazoline portion with a complementary chemical group on the lipid portion. The chemical groups on the polyoxazoline portion and/or the lipid portion may be activated prior to the reaction (such as, but not limited to, removal of any protecting groups). A hydroxyl, amine or carboxyl group may be activated for coupling by monofunctional activating agents, such as N-hydroxysuccinimide, ethylchloroformate, DCCD, Woodward's Reagent K, cyanuric acid and trifluoromethanesulfonyl chloride among others. A number of bifunctional crosslinking reagents containing groups with different reactivities, such as some diisocyanates, may also be used.

To illustrate formation of a polyoxazoline-lipid conjugate of the present disclosure, the scheme below shows conjugation of a POZ NHS ester with pendent acetylene groups as the active functional group with an amino phospholipid (1,2-dipalmitoyl-sn-glycero-3-phosphoethanolamine, DPPE) to form a polyoxazoline-lipid conjugate that contains pendent acetylene groups. The polyoxazoline portion was described as in Example 19 herein and the abbreviations used can be found in Examples 19-22. Additional examples of polyoxazoline-lipid conjugates of the present disclosure are provided in Examples 22-24 herein.

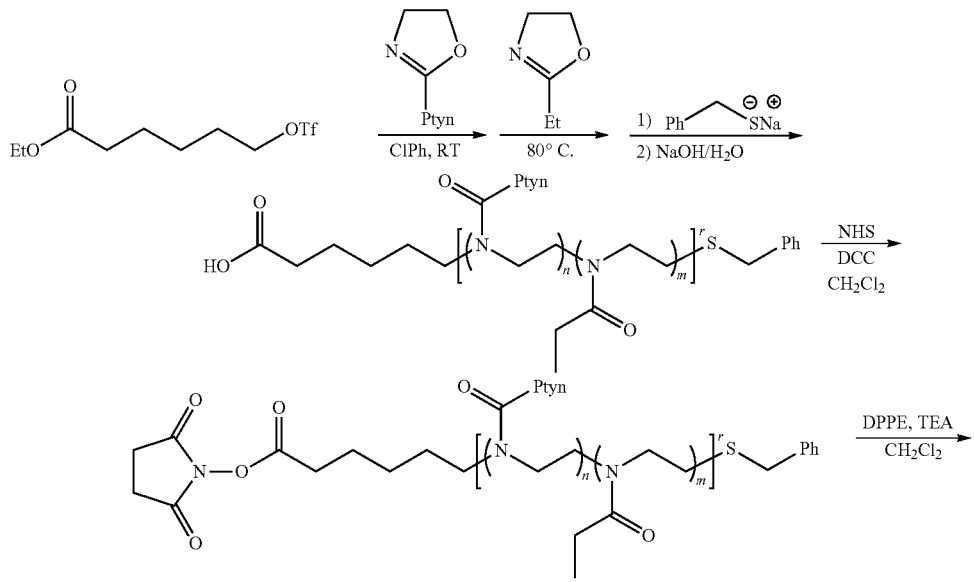

-continued

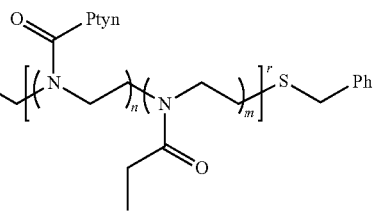
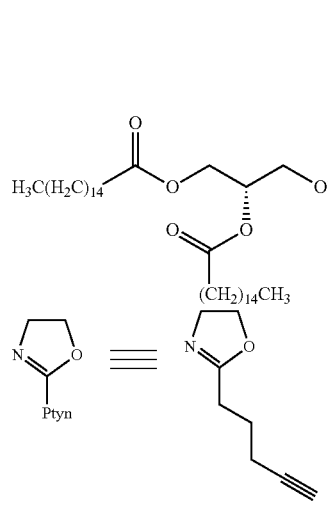

The acetylene groups are suitable for forming a linkage to binding partners on a target molecule, and the polyoxazoline-lipid conjugate can be used to produce liposomal compositions containing at least one polyoxazoline-lipid conjugate.

The art is aware of methods to couple other functional groups. For example, activation of terminal hydroxyl groups is disclosed by (Zalipsky, Biotechnol Appl Biochem. 1992, 15(1):100-14). In one such method, a polyoxazoline polymer with an OH group is reacted with succinic anhydride to generate a carboxyl group. The carboxyl group is activated by reaction with N-hydroxysuccinimide and the polyoxazoline polymer is reacted with an amino group-containing phospholipid.

Liposomal Compositions

Liposomal compositions of the present disclosure incorporating a polyoxazoline-lipid polymer provide a number of advantages over similar liposomal compositions that do not incorporate a polyoxazoline-lipid polymer of the present disclosure. For example, the liposomal compositions of the present disclosure provide a longer residence time for the liposomal composition in the body; as such the liposomal compositions can release entrapped target molecules, such as a therapeutic agent, over a longer period of time. In addition, prolonged residence times allow the liposomal composition to effectively reach various sites in the body and enter such regions.

The polyoxazoline-lipid conjugate of the present disclosure is used in preparing a liposomal composition. In one embodiment, the liposomal composition contains a therapeutic agent for the treatment of human disease. In an alternate embodiment, the liposomal composition contains a diagnostic agent. In still a further embodiment, the liposomal composition contains a targeting agent to target the liposomal composition to a particular cell or tissue. Liposomal compositions of the present disclosure may also contain combinations of the foregoing (for example, a therapeutic agent and a targeting reagent or a diagnostic agent and a targeting agent). In one embodiment the polyoxazoline-lipid conjugate when incorporated in a liposomal composition is present at a mole ratio of about 0.5% to about 50% mole percent in the lipid layer of the liposomal composition, at a mole ratio of about 1% to about 30% mole percent in the lipid layer of the liposomal composition, at a mole ratio of about 2% to about 20% mole percent in the lipid layer of the liposomal composition or at a mole ratio of about 5% to about 10% mole percent in the lipid layer of the liposomal composition. In such embodiment, the polyoxazoline-lipid conjugate may form a layer which is effective to extend the blood circulation time of the liposomes over that of the liposomes lacking the polyoxazoline-lipid conjugate.

The liposomal composition comprises a polyoxazoline-lipid conjugate of the present disclosure in combination with other lipid components (lacking polyoxazoline components) that are capable of forming vesicles and/or liposomes (the lipid components lacking a polyoxazoline component are referred to as underivatized lipids). The underivatized lipids include any amphipathic lipids having hydrophobic and polar head group moieties, and which (a) can form spontaneously into bilayer vesicles in water or (b) are stably incorporated into lipid bilayers, with its hydrophobic moiety in contact with the interior, hydrophobic region of the bilayer membrane, and its polar head group moiety oriented toward the exterior, polar surface of the membrane.

In one embodiment, the underivatized lipid comprises two hydrophobic moieties and a hydrophilic head group. The hydrophobic moieties are typically acyl chains containing an alkyl portion. The alkyl portion of the acyl chain may vary in length; in addition the alkyl portion may be saturated (contain no double bonds) or contain one or more areas of unsaturation (contain one or more double bonds). When unsaturated, the alkyl portion may have varying degrees of unsaturation, for example, from 1 to 4 areas of unsaturation. When the alkyl portion contains an area of unsaturation, the hydrogen atoms at the double bond may be in the cis or trans configuration. In one embodiment, the alkyl portion of the acyl chains contains from 14 to 24 carbons. The alkyl portions of the two hydrophobic moieties may be the same or may be different.

In one embodiment, the underivatized lipid is a phospholipid, a glycerolipid, or a sterol lipid. In a particular embodiment, the underivatized lipid is a phospholipid, such as, but not limited to, a phosphoglyceride or sphingolipid. Exemplary phosphoglycerides include, but are not limited to, phosphatidylcholine, phosphatidylinositol, phosphatidylethanolamine, phosphatidylglycerol, phosphatidylserine and phosphatidic acid; exemplary sphingolipids include, but are not limited to, sphingomyelin. In a specific embodiment, the underivatized lipid is phosphatidylethanolamine.

The polyoxazoline-lipid conjugate of the liposomal composition is prepared as described herein. The polyoxazoline-lipid conjugate is present at a molar concentration sufficient to extend the blood circulation time of the liposomal composition lacking a polyoxazoline-lipid conjugate or to effectively deliver a target molecule to a cell or tissue of the body. In a particular embodiment, the polyoxazoline-lipid conjugate contains at least one polyoxazoline polymer having an active functional group in the pendent position.

The lipid composition is designed to incorporate a target molecule. The target molecule may be entrapped within the liposomal composition in a free form or be linked to the polyoxazoline-lipid conjugate as described herein, or by a combination of the foregoing. A target molecule includes a targeting agent, a diagnostic agent or a therapeutic agent. Exemplary target molecules include, but are not limited to, an organic small molecule, an oligonucleotide, a polypeptide, an antibody, an antibody fragment, a protein, or a carbohydrate. The liposomal composition may contain more than one target molecule. For example, the liposomal composition may have a therapeutic or diagnostic agent entrapped within the liposomal composition and have a targeting agent linked to a polyoxazoline conjugate of the liposomal composition. In this manner the liposomal composition may be targeted to a particular cell or tissue of the body. In one embodiment, at least a portion of the target molecules are exposed to the extra-liposomal environment (such as the bloodstream and cells and tissues of the body).

The size of the liposomes/vesicles in the liposomal composition can vary. In one embodiment, the size is between about 0.025 and about 10 microns; in an alternate embodiment, the size is between about 0.025 microns and about 5 microns; in still a further embodiment, the size is between about 0.025 microns and about 1 micron. Methods of size fractionation are disclosed herein.

The liposomal composition of the present disclosure may be prepared by a variety of methods. In one embodiment, the liposomes are prepared by the reverse-phase evaporation method (Szoka et al. PNAS 1978 vol. 75, 4194-4198; Smirnov et al., Byulleten' Éksperimental'noi Biologii i Meditsiny, 1984, Vol. 98, pp. 249-252; U.S. Pat. No. 4,235,871), In this method, an organic solution of liposome-forming lipids, which may include the polyoxazoline-lipid conjugate, either with or without a linked target molecule, is mixed with a smaller volume of an aqueous medium, and the mixture is dispersed to form a water-in-oil emulsion, preferably using pyrogen-free components. The target molecule to be delivered is added either to the lipid solution, in the case of a lipophilic target molecule, or to the aqueous medium, in the case of a water-soluble target molecule. The lipid solvent is removed by evaporation and the resulting gel is converted to liposomes. The reverse phase evaporation vesicles (REVs) have typical average sizes between about 0.2-0.4 microns and are predominantly oligolamellar, that is, contain one or a few lipid bilayer shells. The REVs may be readily sized, as discussed below, by extrusion to give oligolamellar vesicles having a selected size preferably between about 0.05 to 0.2 microns.

In addition, multilamellar vesicels (MLV's) can be created. In this method, a mixture of liposome-forming lipids, which may include the polyoxazoline-lipid conjugate, either with or without a linked target molecule, as described herein are dissolved in a suitable solvent is evaporated in a vessel to form a thin film. The thin film is then covered, by an aqueous medium. The lipid film hydrates to form MLVs. MLVs generally exhibit sizes between about 0.1 to 10 microns. MLVs may be sized down to a desired size range by extrusion and other method described herein.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka et al. PNAS 1978 vol. 75, 4194-4198). The pore size of the membrane corresponds roughly to the largest sizes of liposomes produced by extrusion through that membrane, particularly where the preparation is extruded two or more times through the same membrane. Process for sizing MLVs of larger sizes is provided by Zhu et al. (*PLoS One*. 2009; 4(4):e5009. Epub 2009 Apr. 6).

When small particle sizes are desired, the REV or MLV preparations can be treated to produce small unilamellar vesicles (SUVs) which are characterized by sizes in the 0.04-0.08 micron range. Such particles may be useful in targeting tumor tissue or lung tissue where the particles may be absorbed through capillary walls (particles larger than 0.1 microns may not be absorbed).

Furthermore, the polyoxazoline-lipid conjugate, either with or without a linked target molecule, may be introduced into the liposomal composition after the liposomes are formed using the techniques described above. In this approach, the preformed liposomes are incubated in the presence of a polyoxazoline-lipid conjugate; the polyoxazoline-lipid conjugate is incorporated into the liposome by diffusion. The concentration of the polyoxazoline-lipid conjugate free in solution or taken up by the liposome may be monitored and the process terminated when a desired concentration of the polyoxazoline-lipid conjugate in the liposomal composition is reached. The incubation solution may contain surfactants or other agents to facilitate diffusion of the polyoxazoline-lipid conjugates into the liposomal composition.

The liposomal composition may be treated to remove extraneous components prior to use. For example, if surfactants are used as discussed above, the excess surfactants may be removed prior to use. In addition where a target molecule, such as therapeutic agent or a diagnostic agent, is entrapped in the liposomal composition, excess or non-entrapped therapeutic agent or diagnostic agent may be removed prior to use. Separation techniques to accomplish this task are known in the art and the particular method selected may depend on the nature of the component to be removed. Exemplary methods include, but are not limited to, centrifugation, dialysis and molecular-sieve chromatography are suitable. The composition can be sterilized by filtration through a conventional 0.45 micron depth filter.

EXAMPLES

Materials and General Methods

Reagents were purchased from EM Science, Acros Organics, ABCR or Aldrich. Dry solvents were prepared by distillation followed by drying by distillation over calcium hydride. Monomers were distilled over calcium hydride or freeze-dried using dry benzene. GPC was performed on an Agilent Technologies instrument with an RI detector. Two Phenogel GPC columns (Phenomenex, 5 microns, 300×7.8 mm) were used in series at 60° C.). The mobile phase was DMF. A calibration curve was generated with M-PEOZ-OH samples of different molecular weights as determined by MALDI TOF. MALDI-TOF MS was performed with a Bruker Microflex or Biflex III with dithranol matrix. The samples were prepared by mixing chloroform solutions of the polymer and matrix (10 mg/mL) in a ratio of 1:1 (v/v). NMR spectra were recorded in $CDCl_3$ on a Bruker ARX-300 or a Varian 500 MHz instrument. EI mass spectra were obtained on a Finigann MAT 8200 at 70 eV.

Example 1

Preparation of 1-(tert-Butyldiphenylsilyl)oxy-dodecan-12-ol (1)

In a Schlenk flask, 1,12-Dodecandiol (7.96 g, 39.4 mmol, 1 eq) was dissolved in 40 mL of dry DMF under nitrogen. Imidazole (2.63 g, 38.6 mmol, 1 eq) and tert-butylchlorodiphenylsilane (TBDPS) (10.84 g, 39.4 mmol, 1 eq) were added and the reaction mixture was heated to 45° C. After stirring for 48 h, the reaction was quenched with 300 mL of distilled water. The aqueous phase was extracted four times with diethyl ether, the organic phases were collected and washed twice with 2N HCl (2×100 mL), once with saturated NaHCO$_3$ (200 mL), once with saturated NaCl (200 mL) and dried over Na$_2$SO$_4$. Column-chromatography over silica gel using 10/1 hexane/ethyl acetate as eluent yielded 7.98 g (46%) of the desired product as a slightly yellowish oil. $^1$H NMR (300.13 MHz): δ (ppm)=1.05 (s, 9H, tert-butyl), 1.26 (br, 16H, —O—CH$_2$—CH$_2$—CH$_2$—CH$_2$—CH$_2$—), 1.58 (m, 4H, —O—CH$_2$—CH$_2$—), 3.65 (m, 4H, —O—CH$_2$—), 7.40 (m, 6H, phenyl), 7.69 (m, 4H, phenyl). $^{13}$C NMR (75.48 MHz): δ (ppm)=19.2, 25.7, 25.8, 25.9, 29.3, 29.4, 29.58, 29.6, 32.6, 32.8, 63.1, 64.0, 127.5, 129.4, 134.1, 135.6.

Example 2

12-(tert-Butyldiphenylsilyl)oxy-dodecyl 1-trifluoromethanesulfonate (2)

A Schlenk flask was loaded with anhydrous K$_2$CO$_3$ (320 mg, 23.4 mmol, 10 eq) under argon atmosphere, followed by (1) (103 mg, 2.34 mmol, 1 eq). A solution of trifluoromethanesulfonic anhydride in 3.2 ml of dry chloroform was added subsequently and the suspension was vigorously stirred. After 16 h the solvent was evaporated in vacuo, followed by the addition of 3 mL of dry chloroform. Filtration through a PTFE syringe filter under protective atmosphere followed by evaporation of the solvent yielded (2) 134 mg (100%) as a colorless liquid. $^1$H NMR (250.13 MHz): δ (ppm)=1.05 (s, 9H, tert-butyl), 1.26 (br, 16H, —CH$_2$—CH$_2$—CH$_2$—CH$_2$—CH$_2$—), 1.56 (m, 2H, —Si—O—CH$_2$—CH$_2$—), 1.83 (m, 2H, F$_3$C—SO$_2$—O—CH$_2$—CH$_2$—), 3.66 (t, 2H, $^3$J=5 Hz, —Si—O—CH$_2$—), 4.53 (t, 2H, $^3$J=6.5 Hz, F$_3$C—SO$_2$—O—CH$_2$—), 7.40 (m, 6H, phenyl), 7.69 (m, 4H, phenyl).

Example 3

10,12-Docosadiyne-1,22-diol (3)

The substance was synthesized according to a procedure reported by Bader and Ringsdorf (*J. Polym. Sci.*, 1982, 20, 1623) starting from 10.3 g 10-undecyn-1-ol (61.2 mmol). The reaction yielded 9.5 g (28.4 mmol, 93%) of the desired product. $^1$H NMR (250.13 MHz): δ (ppm)=1.26 (br, 20H, —CH$_2$—CH$_2$—CH$_2$—CH$_2$—CH$_2$—), 1.54 (m, 8H, —O—CH$_2$—CH$_2$- and —C≡C—CH$_2$—CH$_2$—), 2.24 (t, 4H, $^3$J-=6.8 Hz, —C≡C—CH$_2$—), 3.64 (t, $^3$J=6.7 Hz, HO—CH$_2$—).

Example 4

1-(tert-Butyldiphenylsilyl)oxy-10,12-Docosadiyne-22-ol (4)

This substance was synthesized following the same procedure as for (1) and obtained in comparable yields using 9.40 g of (3) (28.1 mmol) as diol component. 4.25 g of 1-(tert-Butyldiphenylsilyl)oxy-10,12-Docosadiyne-22-ol (7.24 mmol) was obtained in a yield of 26%. $^1$H NMR (250.13 MHz): δ (ppm)=1.05 (s, 9H, tert-butyl), 1.26 (br, 20H, —CH$_2$—CH$_2$—CH$_2$—CH$_2$—CH$_2$—), 1.53 (m, 8H, —O—CH$_2$—CH$_2$— and —C≡CH$_2$—CH$_2$—), 2.24 (t, 4H, $^3$J=6.8 Hz, —C≡C≡CH$_2$—), 3.64 (t, 2H, $^3$J=6.5 Hz, —Si—O—CH$_2$—), 3.65 (t, 2H, $^3$J=6.5 Hz, HO—CH$_2$—), 7.40 (m, 6H, phenyl), 7.69 (m, 4H, phenyl). $^{13}$C NMR (75.48 MHz): δ (ppm)=25.69, 25.72, 26.9, 28.30, 28.34, 28.8, 29.00, 29.04, 29.30, 29.34, 29.4, 32.5, 32.8, 63.1, 64.0, 127.5, 129.5, 134.1, 135.6.

Example 5

22-(tert-Butyldiphenylsilyl)oxy-10,12-docosadiyne-1 trifluoromethanesulfonate (5)

This molecule was synthesized in the same manner as (2) yielding the desired product quantitatively. $^1$H NMR: δ (ppm)=1.05 (s, 9H, tert-butyl), 1.30 (br, 20H, —O—CH$_2$—CH$_2$—CH$_2$—CH$_2$—CH$_2$—), 1.54 (br, 8H, —O—CH$_2$—CH$_2$—, —C≡C—CH$_2$—CH$_2$—), 2.24 (m, 2H, CF$_3$SO$_2$—O—CH$_2$—CH$_2$—), 3.65 (t, 2H, $^3$J=7 Hz, —C≡C—CH$_2$—), 4.53, (t, 2H, $^3$J=7 Hz, F$_3$C—SO$_2$—O—CH$_2$—), 7.40 (m, 6H, phenyl), 7.68 (m, 4H, phenyl). $^{19}$F NMR: δ=−29.31 ppm (—OSO$_2$—CF$_3$). EI-MS: m/z=646.9 [M−tert-butyl]$^+$, 496.9 [M−tert-butyl, —OSO$_2$CF$_3$]$^+$.

Example 6

General Synthetic Procedure for Polymerization

In a schlenk flask under a dry argon atmosphere, 0.23 mmol (1 eq) of a w-TBDPS-protected triflate was dissolved in 6 mL of dry chloroform. 2-methyl-2-oxazoline (587 mg, 6.91 mmol, 30 eq) was added, the reaction mixture was heated to 60° C. and stirred. After 24 h, 212 mg tert-butyl piperazine-1-carboxylate (1.14 mmol, 5 eq) was added and the mixture was stirred for five more hours, followed by the addition of 300 mg K$_2$CO$_3$ and stirring over night. After cooling to room temperature, the solution was precipitated by injection into a ten-fold excess of ice-cold diethyl ether and centrifuged for 15 minutes at 4000 rpm. After decantation of the liquid phase, the solid phase was dried under a gentle flow of air and dissolved in distilled water. Subsequent freeze-drying gave the desired polymer.

Example 7

Preparation of TBDPS—O—(CH$_2$)$_{12}$—[N(COCH$_3$)CH$_2$CH$_2$]$_{35}$—NC$_4$H$_8$N-Boc (6)

The polymer was synthesized from (2) (125 mg, 0.22 mmol, 1 eq) and 2-methyl-2-oxazoline (650 mg, 7.65 mmol, 35 eq). After 40 h cationic polymerization was terminated by addition of tert-butyl piperazine-1-carboxylate (406 mg, 2.18 mmol, 10 eq). Yield: 644 mg (82%). $^1$H NMR: δ (ppm)=1.03 (s, 9H, —S—C(CH$_3$)$_3$), 1.26 (br, 16H, —CH$_2$—CH$_2$—CH$_2$—CH$_2$—CH$_2$—), 1.44 (s, 9H, —CO—O—(CH$_3$)$_3$), 1.54 (br, 4H, —O—CH$_2$—CH$_2$—), 2.07-2.12 (br, 146H, —N—CO—CH$_3$), 3.45 (b, 191H, —N—CH$_2$—CH$_2$—N—), 3.65 (t, 2H, $^3$J=6.75 Hz, —Si—O—CH$_2$—), 7.38 (m, 6H, phenyl), 7.67 (m, 4H, phenyl). MALDI-TOF: M$_n$=3586 g/mol, PDI=1.01.

Example 8

Preparation of TBDPS—O—(CH$_2$)$_{12}$—[N(COCH$_3$)CH$_2$CH$_2$]$_{35}$—NC$_4$H$_8$N-Boc (7)

The polymer was synthesized from (2) (462 mg, 0.81 mmol, 1 eq) and 2-methyl-2-oxazoline (1.23 g, 14.5 mmol, 18 eq). Polymerization was terminated by addition of piperidine (500 mg, 5.87 mmol, 7.25 eq). Yield: 984 mg (57%). $^1$H NMR: δ (ppm)=1.03 (s, 9H, —Si—C(CH$_3$)$_3$), 1.24 (br, 16H, —CH$_2$—CH$_2$—CH$_2$—CH$_2$—CH$_2$—), 1.55 (br, 4H, —O—CH$_2$—CH$_2$—), 1.70 (br, 2H), 1.86 (br, 5H), 2.07-2.14 (br, 53H, —N—CO—CH$_3$), 2.47 (br, 2H), 3.12 (bm, 7H), 3.45 (br, 65H, —N—CH$_2$—CH$_2$—N—), 3.64 (t, 2H, $^3$J=5.5 Hz, —Si—O—CH$_2$—), 7.38 (m, 6H, phenyl), 7.67 (m, 4H, phenyl). MALDI-TOF: M$_n$=1922 g/mol, PDI=1.03.

Example 9

Preparation of TBDPS—O—(CH$_2$)$_{12}$—[N(COCH$_3$)CH$_2$CH$_2$]$_{18}$—OH (8)

The polymer was synthesized from (2) (66 mg, 0.12 mmol, 1 eq) and 2-methyl-2-oxazoline (176 mg, 2.07 mmol, 17 eq) in 2.75 mL of chloroform and terminated by addition of 280 mg potassium carbonate (2.03 mmol, 17 eq) dissolved in a mixture of 2.75 mL water and 5.75 mL methanol. This mixture was heated at 60° C. and stirred over night. The solvent was evaporated and the solid residue was extracted with chloroform (4 mL). Injection into a ten-fold excess of diethyl ether via a PTFE syringe filter and subsequent freeze-drying using water gave 120 mg (51%) of the polymer, $^1$H NMR: δ (ppm)=1.28, (br, 20H, —CH$_2$—CH$_2$—CH$_2$—CH$_2$—CH$_2$—), 1.53 (br, 8H, —O—CH$_2$—CH$_2$- and —C≡C—CH$_2$—CH$_2$—), 2.06-2.13 (b, 95H, —N—CO—CH$_3$), 3.25 (2H, —N—CH$_2$—CH$_2$—N$^{piperazine}$—), 3.49 (br, 60H, —N—CH$_2$—CH$_2$—N—), 3.56 (t, 2H, $^3$J=6.5 Hz, HO—CH$_2$—), 3.64 (t, 2H, $^3$J=6.5 Hz, —Si—O—CH$_2$—), 3.77 (2H, —CH$_2$—CH$_2$—CH$_2$—N—), 7.38 (m, 6H, phenyl), 7.67 (m, 4H, phenyl). MALDI-TOF: M$_n$=1980 g/mol, PDI=1.02.

Example 10

Preparation of TBDPS—O—(CH$_2$)$_{12}$[—N(COCH$_3$)CH$_2$CH$_2$]$_{53}$—NC$_4$H$_8$NH (9)

The polymer was synthesized from (2) (89 mg, 0.17 mmol, 1 eq) and 2-methyl-2-oxazoline (720 mg, 8.46 mmol, 50 eq) in 4.5 mL of chloroform and terminated by injection of a solution of 450 mg piperazine (5.23 mmol, 31 eq) in 3 mL of chloroform at 60° C. Yield: 551 mg (67%). $^1$H NMR: δ=1.03 ppm (s, 9H, —S—C(CH$_3$)$_3$), 1.24 (br, 16H, —CH$_2$—CH$_2$—CH$_2$—CH$_2$—CH$_2$—), 1.54 (br, 4H, —O—CH$_2$—CH$_2$—), 2.07-2.13 (br, 53H, —N—CO—CH$_3$), 2.93 (br, 16H), 3.07 (s, 12H), 3.23 (br, 8H), 3.45 (br, 65H, —N—CH$_2$—CH$_2$—N—), 3.64 (t, 2H, $^3$J=5.5 Hz, —Si—O—CH$_2$—), 7.38 (m, 6H, phenyl), 7.67 (m, 4H, phenyl). MALDI-TOF: M$_n$=4951 g/mol, PDI=1.01.

Example 11

TBDPS—O—(CH$_2$)$_9$—CC—CC—(CH$_2$)$_9$—[N(COCH$_3$)CH$_2$CH$_2$]$_{35}$—NC$_4$H$_8$N-Boc (10)

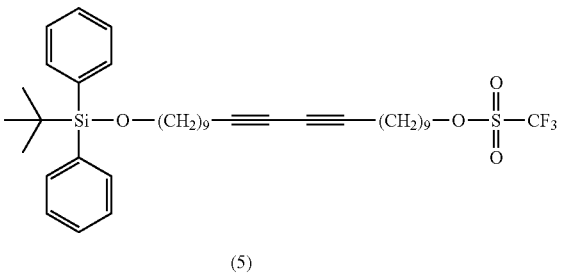

(5)

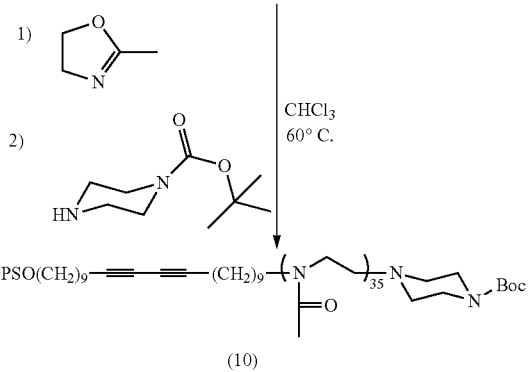

(10)

The polymer was synthesized from (5) (203 mg, 0.29 mmol, 1 eq) and 2-methyl-2-oxazoline (788 mg, 9.26 mmol, 32 eq) in 6 mL of chloroform and terminated with tert-butyl piperazine-1-carboxylate (374 mg, 2.02 mmol, 7 eq). Yield: 699 mg (68%). $^1$H NMR: δ=1.03 ppm (s, 9H, —Si—C(CH$_3$)$_3$), 1.28 (br, 30H, —CH$_2$—CH$_2$—CH$_2$—CH$_2$—CH$_2$—), 1.44-1.46 (m, 33H, —CO—O—C(CH$_3$)$_3$), 1.51 (br, 8H, —O—CH$_2$—CH$_2$- and —C≡C—CH$_2$—CH$_2$—), 2.00 (s, 5H), 2.07-2.13 (br, 53H, —N—CO—CH$_3$), 2.23 (t, 5H $^3$J=5.75 Hz, —C≡C—CH$_2$—), 2.42 (br, 5H), 2.50 (br, 3H), 3.00 (br, 9H), 3.21 (br, 7H), 3.44 (br, 174H, —N—CH$_2$—CH$_2$—N—), 3.61-3.71 (m, 4H, —Si—O—CH$_2$ and HO—CH$_2$—), 7.38 (m, 6H, phenyl), 7.67 (m, 4H, phenyl). MALDI-TOF: M$_n$=3205 g/mol, PDI=1.01.

Example 12

General Procedure for the Deprotection of Tert-Butylcarboxylate and Tert-Butyldiphenylsilyl Protective Groups of Poly(2-Oxazolines)

The tert-butyldiphenylsilyl- and/or tert-butylcarboxylate-protected poly(2-oxazoline) was dissolved in 2N aqueous hydrochloric acid (3 mL/100 mg polymer) and stirred. After 24 hours the resulting suspension was neutralized with NaHCO$_3$, filtrated through cellulose and freeze-dried. The solid residue was extracted with chloroform (3 mL/100 mg polymer) for three hours. The polymer was precipitated by injection into a ten-fold excess of diethyl ether at room temperature. Decantation of the ether phase and subsequent freeze-drying of the solid phase using water gave the desired polymer.

Example 13

Preparation of HO—(CH$_2$)$_{12}$—[N(COCH$_3$)CH$_2$CH$_2$]$_{18}$—OH (11)

The deprotection of (8) (50 mg, 13.9 μmol) yielded 40 mg (88%) of (11). $^1$H NMR: δ=1.26 ppm (br, 16H, —CH$_2$—CH$_2$—CH$_2$—CH$_2$—CH$_2$4, 1.53 (br, 5H, —O—CH$_2$—CH$_2$—), 2.06-2.12 (b, 96H, —N—CO—CH$_3$), 2.33 (br, 13H), 2.47 (br, 4H, —CH$_2$—CH$_2$—NH$^{piperazine}$), 2.87 (br, 3H, CH$_2$—CH$_2$—NH$^{piperazine}$), 3.44 (br, 125H, —N—CH$_2$—CH$_2$—N—), 3.56 (t, 2H, $^3$J=6.5 Hz, —Si—O—CH$_2$—).

Example 14

Preparation of HO—(CH$_2$)$_9$—CC—CC—(CH$_2$)$_9$—[N(COCH$_3$)CH$_2$CH$_2$]$_{35}$—NC$_4$H$_8$NH (12)

Deprotection of (10) (217 mg, 67.7 μmol) yielded 149 mg (77%) of (12). $^1$H NMR: δ=1.28 (br, 30H, —CH$_2$—CH$_2$—CH$_2$—CH$_2$—CH$_2$—), 1.51 (br, 8H, —O—CH$_2$—CH$_2$- and —C≡C—CH$_2$—CH$_2$, 2.06-2.13 (br, 96H, —N—CO—CH$_3$), 2.23 (t, 5H $^3$J=5.75 Hz, —C≡C—CH$_2$—), 2.42 (br, 5H), 2.50 (br, 3H), 3.00 (br, 9H), 3.21 (br, 7H), 3.44 (br, 174H, —N—CH$_2$—CH$_2$—N—).

Example 15

Preparation of the triflate of ethyl 6-hydroxyhexanoate

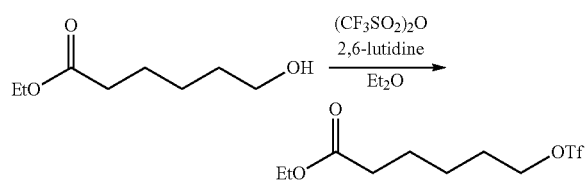

At −10° C., triflic anhydride (4.8 mL, 28.5 mmol) was added dropwise into a solution of 2,6-lutidine (3.31 mL, 28.5 mmol) in diethyl ether (150 mL). After stirring for 15 minutes, ethyl 6-hydroxyhexanoate (4.64 mL, 28.5 mmol) was added dropwise and the resulting mixture was allowed to stir overnight at room temperature. The mixture was filtered and the filtrate was concentrated using rotary evaporation. The crude product was purified by silica gel chromatography (methylene chloride: hexanes=1:1) to afford 4.95 g (65% yield) of the desired product as a yellow oil. $^1$H NMR (Varian, 500 MHz, 10 mg/mL CDCl$_3$): δ 1.27 (t, 7.0 Hz, 3H, —CH$_2$CH$_3$), 1.48 (p, J=7.5 Hz, 2H, TfOCH$_2$CH$_2$CH$_2$CH$_2$—), 1.69 J=7.5 Hz, 2H, TfOCH$_2$CH$_2$CH$_2$CH$_2$4, 1.86 (p, J=7.5 Hz, 2H, TfOCH$_2$CH$_2$CH$_2$CH$_2$—), 2.34 (t, J=7.5 Hz, 2H, —CH$_2$C(=O)OCH$_2$CH$_3$), 4.14 (q, J=7.5 Hz, 2H, —CH$_2$CH$_3$), 4.55 (t, J=6.5 Hz, 2H, TfOCH$_2$CH$_2$—).

Example 16

Preparation of Polymer 13

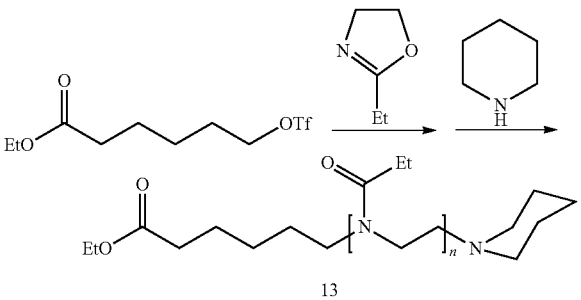

2-Ethyl-2-oxazoline (1.01 mL, 10.0 mmol) was added to a solution of triflate (0.146 g, 0.5 mmol) in chlorobenzene (5 mL). The mixture was heated to 110° C. for 30 minutes, cooled to room temperature, and then terminated by the addition of piperidine (0.2 mL, 2.0 mmol). After stirring for 18 hours at room temperature, the mixture was precipitated by addition to diethyl ether. The ether was decanted and the residue was dried under vacuum to give 0.98 g (99% yield) of product as a white powder. NMR (Varian, 500 MHz, 10 mg/mL CDCl$_3$) shows the usual backbone peaks at 1.12 ppm (s, 3H, CH$_3$CH$_2$CO—); 2.31 ppm (small s) and 2.41 (large s) (total area 2H, CH$_3$CH$_2$CO—); and 3.46 ppm (s, 4H, —NCH$_2$CH$_2$N—). The initiating ethyl hexanoate and the terminating piperidine peaks appear at 1.26 (t, J=7.5 Hz, 3H, CH$_3$CH$_2$OC(=O)—), 1.33 (m, 2H, —CH$_2$CH$_2$CH$_2$CH$_2$N—), 1.45 (m, 2H, —CH$_2$CH$_2$CH$_2$CH$_2$N—), 1.58 (m, 4H, piperidyl-), 1.64 (m, 2H, piperidyl-), 1.69 (m, 2H, —CH$_2$CH$_2$CH$_2$N—), 2.20 (m, 2H, CH$_3$CH$_2$OC(=O)CH$_2$—), 3.23 (m, 2H, —CH$_2$CH$_2$N—), 4.13 (q, J=6.5 Hz, 2H, CH$_3$CH$_2$OC(=O)—). MALDI gave Mn 2260 Da and PD of 1.02.

Example 17

Preparation of Polymer 14

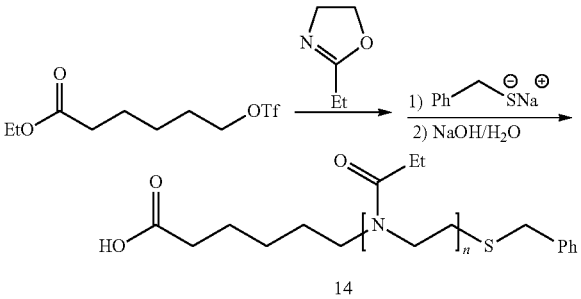

Benzyl mercaptan (0.47 mL, 4.0 mmol) was added dropwise to a suspension of NaH (60% in mineral oil, 0.08 g, 2.0 mmol) in chlorobenzene (4 mL) at 0° C. The mixture was allowed to stir for 3 hours in the cold. 2-Ethyl-2-oxazoline (2.02 mL, 20.0 mmol) was added to a solution of triflate (0.292 g, 1.0 mmol) in chlorobenzene (10 mL). The mixture was heated to 110° C. for 30 minutes, cooled to room temperature, and then added to the flask containing the terminating reagent. After stirring for 18 hours at room temperature, the mixture was precipitated by addition to diethyl ether. The ether was decanted and the residue was dried under vacuum to give 1.42 g of product as a pale yellow powder. NMR (Varian, 500 MHz, 10 mg/mL CDCl$_3$) shows the usual backbone peaks at 1.12 ppm (s, 3H, CH$_3$CH$_2$CO—); 2.30 ppm (small s) and 2.40 (large s) (total area 2H, CH$_3$CH$_2$CO—); and 3.46 Ppm (s, 4H, —NCH$_2$CH$_2$N—). The initiating ethyl hexanoate and terminal benzyl mercaptan peaks appear at 1.27 (t, J=7.5 Hz, 3H, CH$_3$CH$_2$OC(=O)—), 1.33 (m, 2H, —CH$_2$CH$_2$CH$_2$CH$_2$N—), 1.57 (m, 2H, —CH$_2$CH$_2$CH$_2$CH$_2$N—), 1.65 (m, 2H, —CH$_2$CH$_2$CH$_2$CH$_2$N—), 2.17 (m, 2H, CH$_3$CH$_2$OC(=O) CH$_2$—), 2.56 (m, 2H, —CH$_2$SCH$_2$Ar), 3.25 (t, J=7.0 Hz, 2H, —CH$_2$CH$_2$CH$_2$N—), 3.74 (s, 2H, —SCH$_2$Ar), 4.13 (q, J=7.0 Hz, 2H, CH$_3$CH$_2$OC(=O)—), 7.27 (m, 1H, —Ar), 7.33 (m, 5H, —Ar). MALDI gave Mn 2130 Da and PD of 1.04.

Example 18

Deprotection of Polymer 14

Polymer 14 (1.421 g, 0.667 mmol) was dissolved in H$_2$O (60 mL) and then NaOH (0.133 g, 3.33 mmol) was added as a solid. After stirring for 1 hour, the mixture was acidified with 5% aqueous HCl solution and then extracted with dichloromethane three times. The combined organic phases were dried over sodium sulfate, filtered, concentrated, and precipitated by addition to diethyl ether. The ether was decanted and the residue was dried under vacuum to give a pale yellow powder in quantitative yield. NMR (Varian, 500 MHz, 10 mg/mL CDCl$_3$) shows the usual backbone peaks at 1.13 ppm (s, 3H, CH$_3$CH$_2$CO—); 2.32 ppm (small s) and 2.42 (large s) (total area 2H, CH$_3$CH$_2$CO—); and 3.48 ppm (s, 4H, —NCH$_2$CH$_2$N—). The initiating hexanoic acid and the terminal benzyl mercaptan peaks appear at 1.36 (m, 2H, —CH$_2$CH$_2$CH$_2$CH$_2$N—), 1.58-1.65 (m, 4H, —CH$_2$CH$_2$CH$_2$CH$_2$N— and —CH$_2$CH$_2$CH$_2$CH$_2$N—), 2.18 (m, 2H, CH$_3$CH$_2$OC(=O)CH$_2$—), 2.54 (m, 2H, CH$_2$SCH$_2$Ar), 3.31 (t, J=7.0 Hz, 2H, —CH$_2$CH$_2$CH$_2$N—), 3.74 (s, 2H, —SCH$_2$Ar), 7.27 (m, 1H, —Ar), 7.33 (m, 5H, —Ar). Additionally, $^1$H NMR showed the disappearance of proton peaks for the ester group (CH$_3$CH$_2$OC(=O)—) at 1.27 and 4.13 upon the hydrolysis. NMR analysis of the trifluoroacetylated product revealed that the polymer contained 6% of CO$_2$H—PEOZ-OH, formed due to incomplete termination with NaSBz.

Example 19

Preparation of Hexanoate-Initiated POZ with Acetylene Pendent Groups -HA-[(Ptyn)$_2$(Et)$_{20}$]-SBz Benzyl mercaptan (1.47 mL, 12.5 mmol) was added dropwise to a suspension of NaH (60% in mineral oil, 0.30 g, 7.5 mmol) in chlorobenzene (38 mL) at room temperature. The mixture was stirred for 2 hours at room temperature. A solution of 2-(pent-4-ynyl)-2-oxazoline (PtynOZ, 0.686 g, 5.0 mmol) in chlorobenzene (5 mL) was added to a solution of ethyl hexanoate-triflate (0.731 g, 2.5 mmol) in chlorobenzene (20 mL) and the resulting mixture was stirred for 10 minutes at room temperature. 2-Ethyl-2-oxazoline (5.05 mL, 50.0 mmol) was added and the mixture was heated to 80° C. for 90 minutes, cooled to room temperature, and then added to the flask containing the terminating reagent using a cannula. After stirring for 18 hours at room temperature, the mixture was precipitated by addition to diethyl ether. The precipitate was collected using a frit and dried under vacuum to give 4.37 g of product as a pale yellow powder. NMR (Varian, 500 MHz, 10 mg/mL CDCl$_3$) shows the usual backbone peaks at 1.12 ppm (s, 3H, CH$_3$CH$_2$CO—); 2.30 ppm (small s) and 2.40 (large s) (total area 2H, CH$_3$CH$_2$CO—); and 3.46 ppm (s, 4H, —NCH$_2$CH$_2$N—). The initiating ethyl hexanoate and terminal thiobenzyl peaks appear at 1.26 ppm (t, J=7.5 Hz, 3H, CH$_3$CH$_2$OC(=O)—); 1.33 ppm (m, 2H, —CH$_2$CH$_2$CH$_2$CH$_2$N—); 1.57 ppm (m, 2H, —CH$_2$CH$_2$CH$_2$CH$_2$N—); 1.65 ppm (m, 2H, —CH$_2$CH$_2$CH$_2$CH$_2$N—); 2.17 ppm (m, 2H, CH$_3$CH$_2$OC(=O)CH$_2$—); 2.56 ppm (m, 2H, —CH$_2$SCH$_2$Ar); 3.25 ppm (t, J=7.0 Hz, 2H, —CH$_2$CH$_2$CH$_2$N—); 3.74 ppm (s, 2H, —SCH$_2$Ar); 4.13 ppm (q, J=7.0 Hz, 2H, CH$_3$CH$_2$OC(=O)—); 7.27 ppm (m, 1H, —Ar); and 7.33 ppm (m, 5H, —Ar). The pendent group peaks show at 1.83 ppm (m, 2H, —CH$_2$CH$_2$C≡CH); and 2.00 ppm (m, 1H, —CH$_2$CH$_2$C≡CH). The ratio of pentynyl and EOZ was determined as 1.88:20. GPC gave Mn=1960 Da and Mp=2100 Da with PDI of 1.07, MALDI gave Mn 2380 Da and PD of 1.05.

The ethyl hexanoate polymer (0.42 g, 0.214 mmol) was dissolved in aqueous NaOH solution (10 mL, pH 13) and stirred for 1 hour. The mixture was acidified (pH 3), charged with NaCl (15 w/w %), and extracted with dichloromethane. The combined organic phases were dried over Na$_2$SO$_4$, filtered, concentrated, and precipitated by addition to diethyl ether. The precipitates were filtered using a frit and dried under vacuum to give 0.39 g of product as a white powder. NMR (Varian, 500 MHz, 10 mg/mL CDCl$_3$) shows the usual

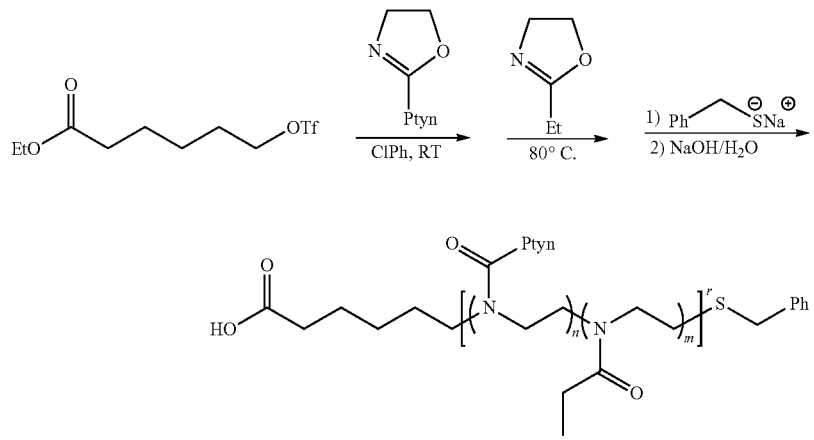

backbone peaks at 1.12 ppm (s, 3H, CH$_3$CH$_2$CO—); 2.32 ppm (small s) and 2.42 (large s) (total area 2H, CH$_3$CH$_2$CO—) and 3.48 ppm (s, 4H, —NCH$_2$CH$_2$N—). The initiating hexanoic acid and the terminal thiobenzyl peaks appear at 1.37 ppm (m, 2H, —CH$_2$CH$_2$CH$_2$CH$_2$N—); 1.58-1.65 ppm (m, 4H, —CH$_2$CH$_2$CH$_2$CH$_2$N— and —CH$_2$CH$_2$CH$_2$CH$_2$N—); 2.17 ppm (m, 2H, CH$_3$CH$_2$OC(=O)CH$_2$—); 2.55 ppm (m, 2H, —CH$_2$SCH$_2$Ar); 3.31 ppm (br s, 2H, —CH$_2$CH$_2$CH$_2$N—); 3.75 ppm (s, 2H, —SCH$_2$Ar); 7.27 ppm (m, 1H, —Ar) and, 7.34 ppm (m, 5H, —Ar). The pendent group peaks show at 1.85 ppm (m, 2H, —CH$_2$CH$_2$C≡CH), and 2.00 ppm (m, 1H, —CH$_2$CH$_2$C≡CH). Additionally, $^1$H NMR showed the disappearance of proton peaks for the ester group (CH$_3$CH$_2$OC(=O)—) at 1.26 ppm and 4.13 ppm upon the hydrolysis. GFC showed 70% of polymers contain CO$_2$H— functionality at the beginning of the polymers. GPC gave Mn=1900 Da and Mp=2050 Da with PDI of 1.07. Chromatography on DEAF Sepharose gives pure acid.

Example 20

Preparation of a Hexanoate-Initiated POZ with Pendent Acetylenes and Terminal Amine -HA-[(Ptyn)$_2$(Et)$_{20}$]-T-NHBoc

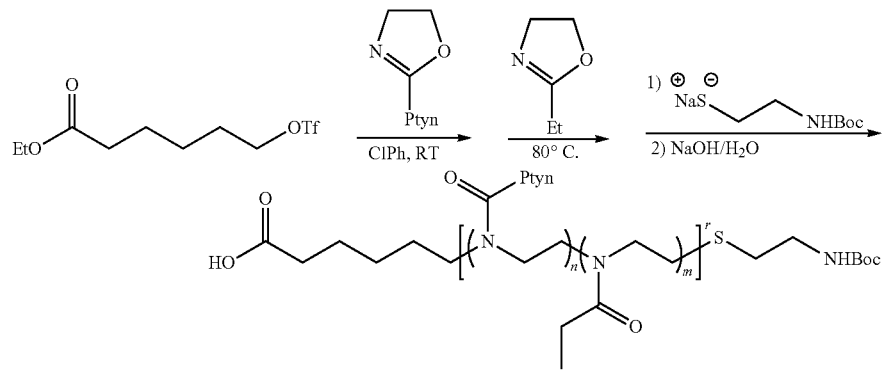

t-Boc cysteamine (2.11 mL, 12.5 mmol) was added dropwise to a suspension of NaH (60% in mineral oil, 0.30 g, 7.5 mmol) in chlorobenzene (38 mL) at room temperature. The mixture was stirred for 2 hours at room temperature. A solution of 2-(pent-4-ynyl)-2-oxazoline (PtynOZ, 0.686 g, 5.0 mmol) in chlorobenzene (5 mL) was added to a solution, of ethyl hexanoate-triflate (0.731 g, 2.5 mmol) in chlorobenzene (20 mL) and the resulting mixture was stirred for 10 minutes at room temperature. 2-Ethyl-2-oxazoline (5.05 mL, 50.0 mmol) was added and the mixture was heated to 80° C. for 90 minutes, cooled to room temperature, and then added to the flask containing the terminating reagent using a cannula. After stirring for 18 hours at room temperature, the mixture was precipitated by addition to diethyl ether. The precipitates were filtered using a frit and dried under vacuum to give 4.71 g of product as a pale yellow powder. NMR (Varian, 500 MHz, 10 mg/mL CDCl$_3$) shows the usual backbone peaks at 1.12 ppm (s, 3H, CH$_3$CH$_2$CO—); 2.30 ppm (small s) and 2.40 (large s) (total area 2H, CH$_3$CH$_2$CO—) and 3.46 ppm (s, 4H, —NCH$_2$CH$_2$N—). The initiating ethyl hexanoate and terminal group peaks appear at 1.26 ppm (t, J=7.5 Hz, 3H, CH$_3$CH$_2$OC(=O)—); 1.33 ppm (m, 2H, —CH$_2$CH$_2$CH$_2$CH$_2$N—); 1.44 ppm (s, 9H, —NHBoc); 1.59 ppm (m, 2H, —CH$_2$CH$_2$CH$_2$CH$_2$N—); 1.66 ppm (m, 2H, —CH$_2$CH$_2$CH$_2$CH$_2$N—); 2.17 ppm (m, 2H, CH$_3$CH$_2$OC(=O)CH$_2$—); 2.67 ppm (m, 2H, —SCH$_2$CH$_2$NHBoc); 2.71 ppm (m, 2H, —CH$_2$SCH$_2$CH$_2$NHBoc); 3.32 ppm (m, 2H, —SCH$_2$CH$_2$NHBoc); and 4.13 ppm (q, J=7.0 Hz, 2H, CH$_3$CH$_2$OC(=O)—). The pendent group peaks appear at 1.84 ppm (m, 2H, —CH$_2$CH$_2$C≡CH) and 2.01 ppm (m, 1H, —CH$_2$CH$_2$C≡CH). The ratio of pentynyl and EOZ was determined as 1.9:20. GPC gave Mn=2090 Da and Mp=2200 Da with PDI of 1.06. MALDI gave Mn 2620 Da and PD of 1.05.

The ethyl hexanoate polymer (0.42 g, 0.201 mmol) was dissolved in aqueous NaOH solution (10 mL, pH 13) and stirred for 1 hour. The mixture was acidified (pH 3), charged with NaCl (15 w/w %), and extracted with dichloromethane. The combined organic phases were dried over Na$_2$SO$_4$, filtered, concentrated, and precipitated by addition to diethyl ether. The precipitates were filtered using a frit and dried under vacuum to give 0.39 g of product as a white powder. NMR (Varian, 500 MHz, 10 mg/mL CDCl$_3$) shows the usual backbone peaks at 1.12 ppm (s, 3H, CH$_3$CH$_2$CO—); 2.30 ppm (small s) and 2.40 (large s) (total area 2H, CH$_3$CH$_2$CO—) and 3.46 ppm (s, 4H, —NCH$_2$CH$_2$N—). The initiating hexanoic acid and terminal group peaks appear at 1.37 ppm (m, 2H, —CH$_2$CH$_2$CH$_2$CH$_2$N—); 1.44 ppm (s, 9H, —NHBoc); 1.61 ppm-1.72 ppm (m, 4H, —CH$_2$CH$_2$CH$_2$CH$_2$N— and —CH$_2$CH$_2$CH$_2$CH$_2$N—); 2.17 ppm (m, 2H, HO$_2$C(=O)CH$_2$—); 2.67 ppm (m, 2H, —SCH$_2$CH$_2$NHBoc); 2.71 ppm (m, 2H, —CH$_2$SCH$_2$CH$_2$NHBoc) and 3.32 ppm (m, 2H, —SCH$_2$CH$_2$NHBoc). The pendant group peaks appear at 1.85 ppm (m, 2H, —CH$_2$CH$_2$C≡CH) and 2.01 ppm (m, 1H, —CH$_2$CH$_2$C≡CH). Additionally, $^1$N NMR showed the disappearance of proton peaks for the ester group (CH$_3$CH$_2$OC(=O)—) at 1.26 and 4.13 upon the hydrolysis. GFC showed 70% of polymers contain CO$_2$H— functionality at the initiator end of the polymers. GPC gave Mn=2040 Da and Mp=2180 Da with PDI of 1.06. Chromatography on DEAF Sepharose gives pure acid.

Example 21

Preparation of POZ with Pendent Acetylenes and Inert Terminus H-[(Ptyn)₂(Et)₂₀]-SBz

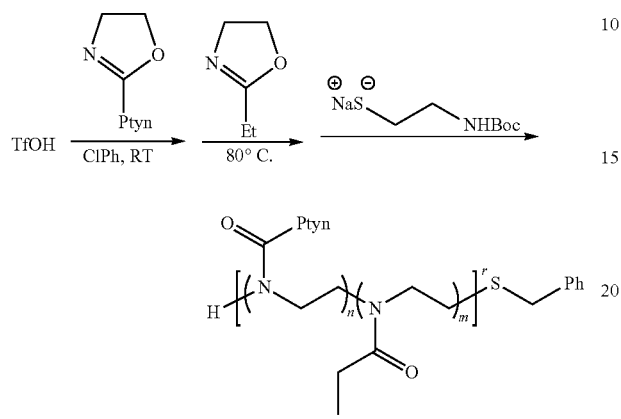

Benzyl mercaptan (1.18 mL, 10.0 mmol) was added dropwise to a suspension of NaH (60% in mineral oil, 0.24 g, 6.0 mmol) in chlorobenzene (30 mL) at room temperature. The mixture was stirred for 2 hours at room temperature. Triflic acid (HOTf, 0.177 mL, 0.002 mol) was added into a solution of 2-(pent-4-ynyl)-2-oxazoline (PtynOZ, 0.686 g, 5.0 mmol) in chlorobenzene (20 mL) and the resulting mixture was stirred for 10 minutes at room temperature. 2-Ethyl-2-oxazoline (4.04 mL, 40.0 mmol) was added and the mixture was heated to 80° C. for 90 minutes, cooled to room temperature, and then added to the flask containing the terminating reagent using a cannula. After stirring for 18 hours at room temperature, the mixture was precipitated by addition to diethyl ether. The precipitate was filtered using a frit and dried under vacuum to give 3.64 g of product as a white powder. NMR (Varian, 500 MHz, 10 mg/mL CDCl₃) shows the usual backbone peaks at 1.12 ppm (s, 3H, CH₃CH₂CO—); 2.29 ppm (small s) and 2.40 (large s) (total area 2H, CH₃CH₂CO—); and 3.46 ppm (s, 4H, —NCH₂CH₂N—). The terminal thiobenzyl peaks appear at 2.56 ppm (m, 2H, —CH₂SCH₂Ar); 3.32 ppm (m, 2H, —CH₂CH₂CH₂N—), 3.74 ppm (s, 2H, —SCH₂Ar); 7.27 ppm (m, 1H, —Ar); and 7.33 ppm (m, 5H, —Ar). The pendent group peaks appear at 1.84 ppm (m, 2H, —CH₂CH₂C≡CH); and 2.00 ppm (m, 1H, —CH₂CH₂C≡CH). The ratio of pentynyl and EOZ was determined as 1.85:20. GPC gave Mn=2150 Da and Mp=2280 Da with PDI of 1.09.

Example 22

Synthesis of M-PEOZ-DSPE

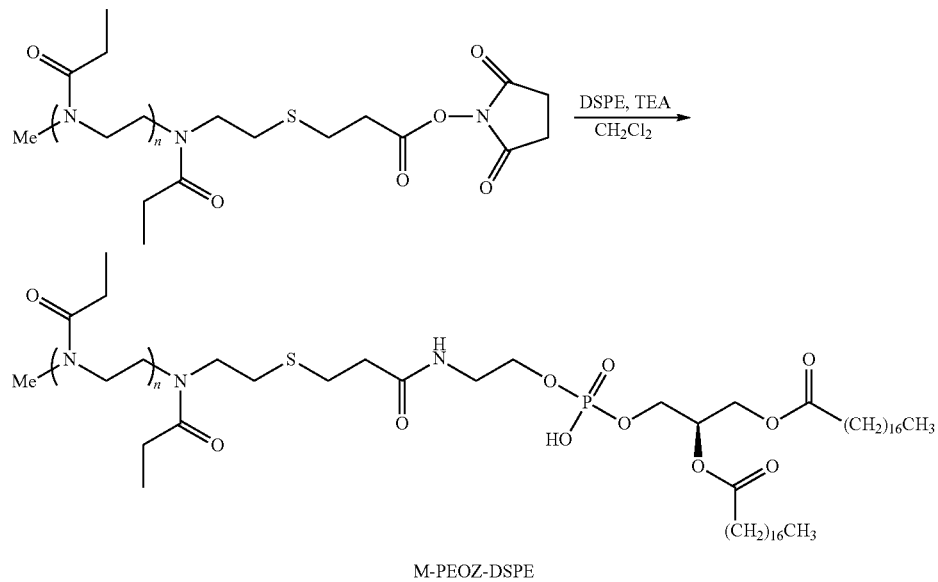

M-PEOZ-DSPE

M-PEOZ-T-SPA (Mn 5050 Da, 70.0 mg, 0.0139 mmol) and 1,2-distearoyl-sn-glycero-3-phosphoethanolamine (DSPE, 15.6 mg, 0.0208 mmol) were dissolved in dichloromethane (5 mL). After addition of TEA (5.8 µL, 0.0416 mmol), the resulting mixture was stirred for 16 hours at room temperature. The mixture was stirred with Na₂CO₃ (102 mg, 0.964 mmol) for 30 minutes and filtered. The filtrate was concentrated and precipitated by addition into diethyl ether. The diethyl ether solution was decanted and the remaining white powdery material was dried in vacuo to give the desired product, M-PEOZ-DSPE (72.0 mg, 91%). The conjugation of DSPE was demonstrated by MALDI giving Mn 5470 Da and ¹H NMR spectra that show the terminal DSPE protons at 0.87 (t, 6H), 3.97 (m, 4H), 4.16 (m, 1H), 4.38 (m, 1H), 5.22 (m, 1H) besides the usual backbone peaks and the aliphatic proton peaks from alkyl chains. HPLC (ZORBAX 300SB-C3 reverse phase column) showed a substitution yield of 92%.

Example 23

Synthesis of M-PEOZ-DPPE

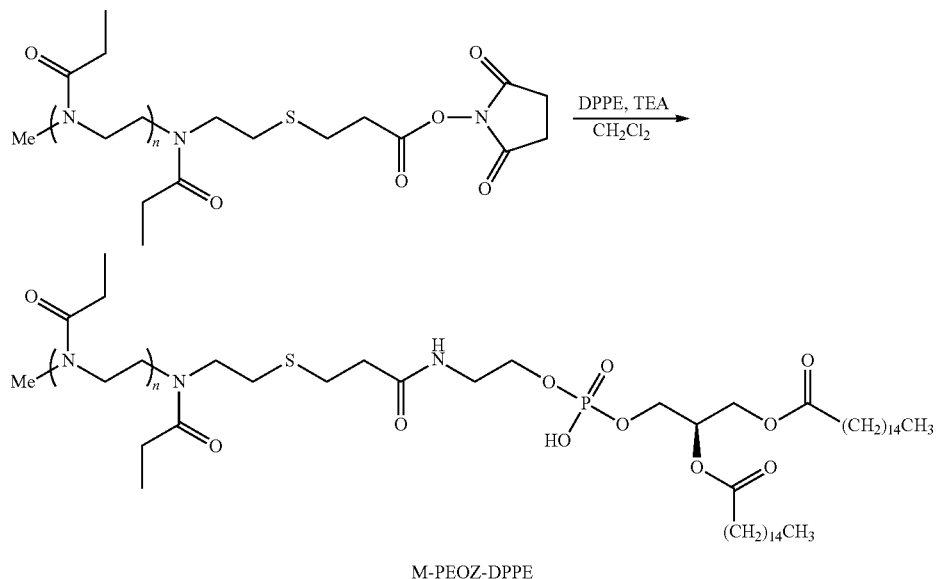

M-PEOZ-DPPE

M-PEOZ-T-SPA (Mn 5050 Da, 70.0 mg, 0.0139 mmol) and 1,2-dipalmitoyl-sn-glycero-3-phosphoethanolamine (DPPE, 14.4 mg, 0.0208 mmol) were dissolved in dichloromethane (5 mL). After addition of TEA (5.8 µL, 0.0416 mmol), the resulting mixture was stirred for 16 hours at room temperature. The mixture was stirred with $Na_2CO_3$ (102 mg, 0.964 mmol) for 30 minutes and filtered. The filtrate was concentrated and precipitated by addition into diethyl ether. The diethyl ether solution was decanted and the remaining white powdery material was dried in vacuo to give the desired product, M-PEOZ-DPPE (69.0 mg, 89%). The conjugation of DPPE was proved by MALDI giving Mn 5530 Da and $^1$H NMR spectra that show the terminal DPPE protons at 0.87 (t, 6H), 3.98 (m, 4H), 4.16 (m, 1H), 4.38 (m, 1H), 5.22 (m, 1H) besides the usual backbone peaks and the aliphatic proton peaks from alkyl chains. HPLC (ZORBAX 300SB-C3 reverse phase column) showed a substitution yield of 99%.

Example 24

Synthesis of H-[(Ptyn)$_5$(Et)$_{50}$]-DPPE

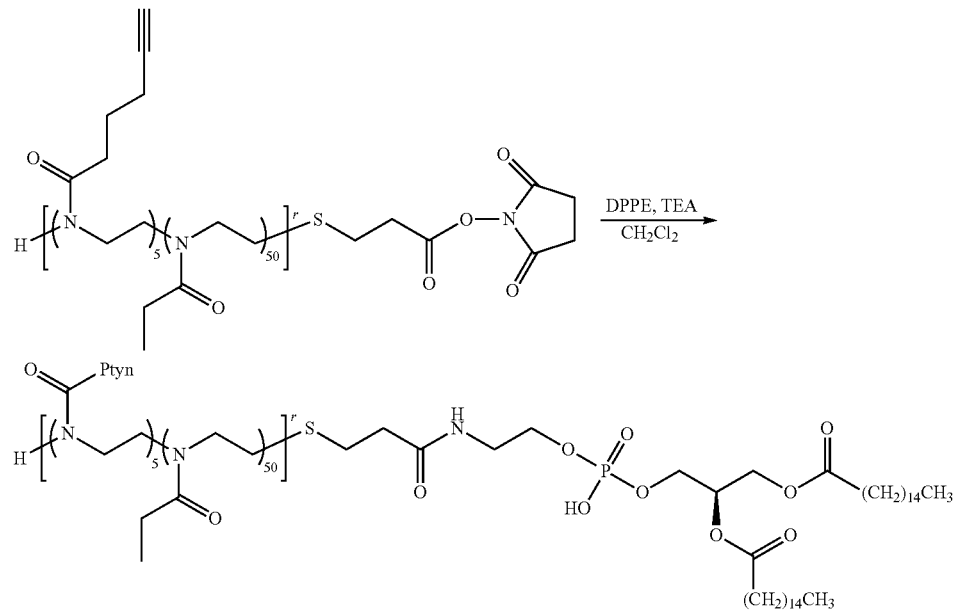

H—[(Ptyn)$_5$(Et)$_{50}$]—DPPE

H-[(Ptyn)$_5$(Et)$_{50}$]-T-SPA (Mn 5747 Da, 91.3 mg, 0.0159 mmol) and 1,2-dipalmitoyl-sn-glycero-3-phosphoethanolamine (DPPE, 16.5 mg, 0.0238 mmol) were dissolved in chloroform (4 mL). After the addition of TEA (6.64 µL, 0.0477 mmol), the resulting mixture was stirred for 16 hours at room temperature. The mixture was stirred with Na$_2$CO$_3$ (102 mg, 0.964 mmol) for 30 minutes and filtered. The filtrate was concentrated and precipitated by addition into diethyl ether. The precipitated solution was filtered using a frit and dried in vacuo to give the desired product, H-[(Ptyn)$_5$(Et)$_{50}$]-DPPE (92.3 mg, 92%). The conjugation of DPPE was proved by MALDI giving Mn 6492 Da and $^1$H NMR spectra that show the terminal DPPE protons at 0.87 (t, 6H), 4.12 (m, 4H), 4.16 (m, 1H), 4.35 (m, 1H), 5.24 (m, 1H) besides the usual backbone peaks and the aliphatic proton peaks from alkyl chains, HPLC (ZORBAX 300SB-C3 reverse phase column) showed a substitution yield of 99.7%.

Example 25

Preparation of a 2 kDa Poly(2-Ethyl)Oxazoline Cholesterol Conjugate with a Fluorescein Marker

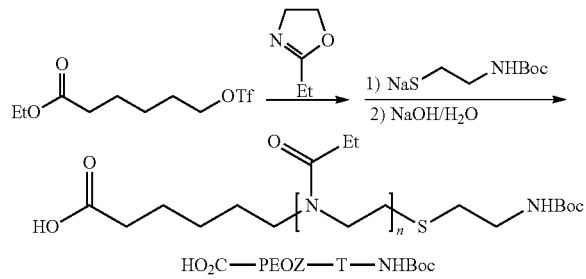

2-Ethyl-2-oxazoline (8.08 mL, 80.0 mmol) was added to a solution of ethyl hexanoic triflate (1.169 g, 4.00 mmol) in chlorobenzene (40 mL). The mixture was heated to 110° C. for 30 minutes and then cooled down to room temperature. In a separate flask, the terminating reagent was prepared. Boc-cysteamine (3.38 mL, 20.0 mmol) was added dropwise into a suspension of sodium hydride (60% in mineral oil, 0.48 g, 80.0 mmol) in chlorobenzene (24 mL) at room temperature. After this mixture was stirred for 2 hours in the cold, the solution of living polymer species in chlorobenzene (from 1$^{st}$ flask) was transferred into the Boc-cysteamine termination mixture. This mixture was stirred for an additional 16 hours at room temperature and then precipitated by addition to diethyl ether. The ether solution was filtered, and the precipitate was dried to give 9.03 g of polymer having ethyl ester and —NH-Boc as the terminal groups. Analytical results by GPC showed a Mn=2260 Da and Mp=2390 Da with PDI of 1.03; MALDI showed a Mn 2140 Da and PD of 1.04.

The precipitate was next dissolved in water and the pH was adjusted to 12 by the addition of sodium hydroxide solution. After stirring for 1 hour, the mixture was acidified (pH ~3) and purified by ion-exchange chromatography (DEAF Sepharose FF) to give the desired product (HO$_2$C-PEOZ-T-NHBoc, 2K) as a white powder (5.3 g, 59% yield). Analytical results of the product: $^1$H NMR (Varian, 500 MHz; 10 mg/mL CDCl$_3$) showed the usual backbone peaks at 1.13 ppm (m, 3H, CH$_3$CH$_2$CO—); 2.32 ppm (m) and 2.41 (s) (total area 2H, CH$_3$CH$_2$CO—); and 3.47 ppm (m, 4H, —NCH$_2$CH$_2$N—). The terminal group peaks appear at 1.35 ppm (m, 2H, HO$_2$CCH$_2$CH$_2$CH$_2$CH$_2$CH$_2$—), 1.61 (m, 4H, HO$_2$CCH$_2$CH-2CH$_2$CH$_2$CH$_2$—), 2.69 ppm (m, 4H, —CH$_2$SCH$_2$CH$_2$NHBoc), and 3.31 ppm (m, 2H, HO$_2$CCH$_2$CH$_2$CH$_2$CH$_2$CH$_2$—, and 2H, —SCH$_2$CH$_2$NHBoc); MALDI gave a Mn 2063 Da and PD of 1.03.

A solution of cholesteryl chloroformate (5.00 g, 11.1 mmol) in dichloromethane (40 mL) was added dropwise into a solution of ethylene diamine (14.9 mL, 223 mmol) in dichloromethane (110 mL) at −5° C. After stirring for 30 minutes in the cold, most of the volatiles were removed using a rotary evaporator. The residue was dissolved in dichloromethane and washed with saturated NaHCO$_3$ aqueous solution followed by a brine solution. The resulting solution was dried over Na$_2$SO$_4$, filtered and concentrated using a rotary evaporator. The crude mixture was purified by recrystallization using ethanol to give 3.4 g of cholesteryl 2-aminoethyl-carbamate as a white powder in 65% yield. $^1$H NMR (Varian, 500 MHz, 10 mg/mL CDCl$_3$) showed aminoethyl proton peaks at 2.80 ppm (t, J=6.0 Hz, 2H, —OC(=O)NHCH$_2$CH$_2$NH$_2$) and 3.21 ppm (m, 2H, —OC(=O)NHCH$_2$CH$_2$NH$_2$) along with the peaks corresponding to the cholesteryl group.

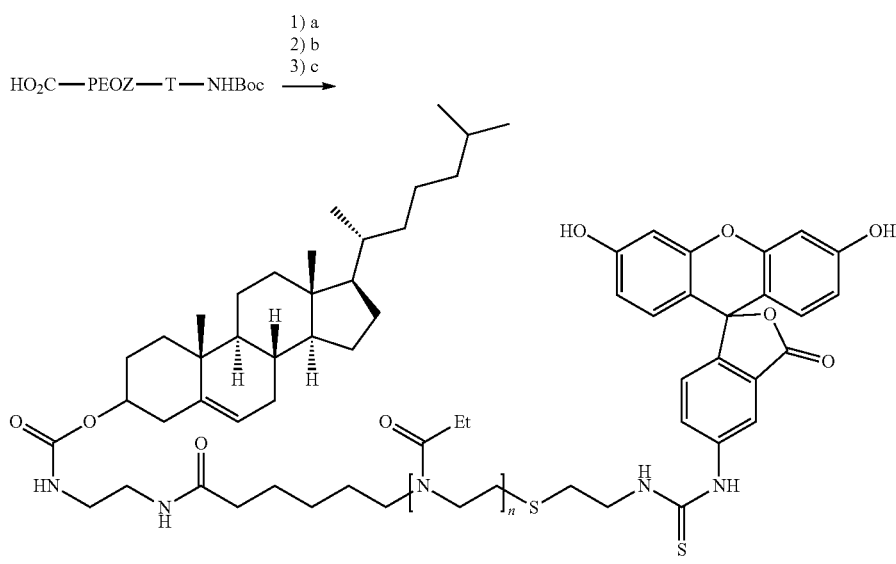

a) DCC, HOBT, cholesteryl 2-aminoethylcarbamate; b) 3N methanolic HCl; c) fluorescein isothiocyanate, isomer I HOBT (0.298 g, 2.21 mmol), dried by azeotropic distillation using acetonitrile (15 mL), and HO₂C-PEOZ-T-NHBoc (Mn 2063 Da, 2.0 g, 0.969 mmol) were dissolved in dichloromethane (15 mL). After the addition of DCC (0.273 g, 1.32 mmol), the mixture was stirred for 2.5 hours at room temperature. Cholesteryl 2-aminoethylcarbamate was added and the resulting mixture was allowed to stir for 18 hours at room temperature. The mixture was filtered using a filter paper into diethyl ether to get white precipitate. The ether solution was decanted. The resulting white precipitate was redissolved in dichloromethane and reprecipitated by addition to diethyl ether. The ether was decanted and the residue was dried under vacuum to provide the desired product (Chol-PEOZ-T-NH-Boc). ¹NMR showed the relative integral ratio of terminal Boc group and cholesteryl group as 1:1.

The Chol-PEOZ-T-NHBoc product was next dissolved in 3N methanolic HCl (80 mL) and stirred for 1 hour at room temperature. Most of the volatiles were removed using a rotary evaporator. The residue, was dissolve in water and then pH value was adjusted to 10. The aqueous solution was charged with NaCl (15% w/v) and extracted twice with dichloromethane. The combined organic phases were dried over Na₂SO₄, filtered, concentrated, and dried in vacuo to provide 1.95 g of the desired product (Chol-PEOZ-T-NH₂) in 83% yield. The deprotection of -Boc group was confirmed by ¹N NMR showing the disappearance of the proton peak for -Boc group at 1.43 ppm.

Fluorescein isothiocyanate (0.054 g, 0.139 mmol) was added into a solution of Chol-PEOZ-NH₂ (Calc. Mn 2517 Da, 0.3 g, 0.119 mmol) in DMF (5 mL). After the addition of triethylamine (39 μL, 0.277 mmol), the mixture was stirred for 18 hours at room temperature in the dark. Most of the volatiles were removed in vacuo and the residue was redissolved in water at pH 9.0. After the pH was adjusted to 3.0, the mixture was extracted with dichloromethane. The extracts were dried over Na₂SO₄, filtered, concentrated, and dried in vacuo to give 0.31 g of yellow powder in 90% yield.

The foregoing description illustrates and describes certain embodiments of the compounds and applications of the present disclosure. Additionally, the disclosure shows and describes only the exemplary embodiments of the compounds and applications, but as mentioned above, it is to be understood that the teachings of the present disclosure are capable of use in various other combinations, modifications, and environments and is capable of changes or modifications within the scope of the concepts as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All references cited herein are incorporated by reference as if fully set forth in this disclosure.

What is claimed:

1. A polyoxazoline-phospholipid conjugate comprising a lipid portion linked to a polyoxazoline portion having the structure: -L$_I$-{POZ$_I$-POZ$_{II}$}$^a$-S-L$_{II}$-R* or I-{POZ$_I$-POZ$_{II}$}$^a$-S-L$_{II}$;

wherein

POZ$_I$ is a polyoxazoline polymer of the structure —[N(CO—R'—Z)CH₂CH₂]$_m$;

POZ$_{II}$ is a polyoxazoline polymer of the structure —[N(COR₂)CH₂CH₂]$_n$;

R', L$_I$, and L$_{II}$ are each optional linking groups;

Z is an active functional group or a group capable of being converted to an active functional group, the active functional group capable of forming a linkage with a binding partner on a target molecule;

R₂ is independently selected for each repeating unit of the polyoxazoline polymer from an unsubstituted or substituted alkyl, alkenyl, aralkyl or heterocycylalkyl group;

R* is an unsubstituted or substituted alkyl, alkenyl, aralkyl, heterocycylalkyl group or an active functional group or a group capable of being converted to an active functional group, the active functional group capable of forming a linkage with a binding partner on a target molecule;

I' is a group present at the initiator position;

n is an integer from 0-1000, provided that when n=0, then m is >1;

m is an integer 1-1000; and a is ran, which indicates a random copolymer, or block, which indicates a block copolymer.

2. The polyoxazoline-phospholipid conjugate of claim 1, wherein at least one of Z and R* is independently an alkyne, an oxyamine, an aldehyde, a ketone, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or an orthopyridyl disulfide.

3. The polyoxazoline-phospholipid conjugate of claim 1, wherein the lipid portion comprises two hydrophobic moieties and a hydrophilic moiety and the lipid portion is linked to the polyoxazoline portion at the hydrophilic moiety.

4. The polyoxazoline-phospholipid conjugate of claim 1, wherein the lipid portion of the polyoxazoline-phospholipid conjugate is a phospholipid or a glycolipid.

5. The polyoxazoline-phospholipid conjugate of claim 1, wherein the lipid portion is a phospholipid and the polyoxazoline-phospholipid conjugate has the general structure:

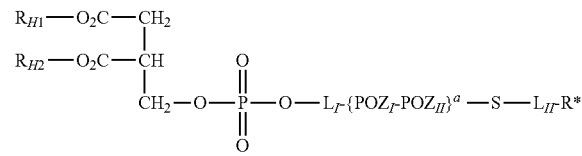

wherein

R$_{H1}$ and R$_{H2}$ are each independently saturated alkyl groups or unsaturated alkyl groups.

6. The polyoxazoline-phospholipid conjugate of claim 5, wherein R* is an alkyne, an oxyamine, an aldehyde, a ketone, an acetal, a ketal, an ester, a carboxylic acid, an activated carboxylic acid, an active carbonate, a chloroformate, an alcohol, an azide, a hydrazide, an amine, a protected amine, a thiol, a vinyl sulfone, a maleimide or an orthopyridyl disulfide.

7. The polyoxazoline-phospholipid conjugate of claim 5, wherein R* is an inert group.

8. The polyoxazoline-phospholipid conjugate of claim 1, wherein the lipid portion is a phospholipid and the polyoxazoline-phospholipid conjugate has the general structure:

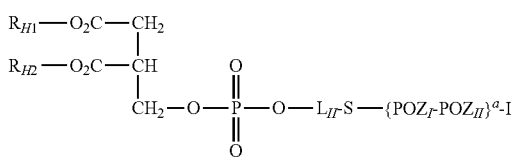

wherein
$R_{H1}$ and $R_{H2}$ are each independently saturated alkyl groups or unsaturated alkyl groups.

9. The polyoxazoline-phospholipid conjugate of claim 8, wherein I is an inert initiating group selected from the group consisting of H and alkyl.

10. The polyoxazoline-phospholipid conjugate of claim 5, wherein $L_I$ and $L_{II}$ are each independently selected from the group consisting of: —$(CH_2)_f$—NHCO—$(CH_2)_g$—, —$(CH_2)_f$—NHCO_2—$(CH_2)_g$— and —$(CH_2)_h$— wherein f, g and h are each an integer independently selected from 0-10.

11. The polyoxazoline-phospholipid conjugate of claim 5, wherein $R_{H1}$ and $R_{H2}$ are each independently C14 to C24 saturated alkyl groups or C14 to C24 unsaturated alkyl groups.

12. The polyoxazoline-phospholipid conjugate of claim 1, wherein the conjugated is contained in a liposome, the liposome comprising a vesicle forming lipid and having a size from about 0.025 microns to about 10 microns.

13. The polyoxazoline-phospholipid conjugate of claim 12, wherein the polyoxazoline-phospholipid conjugate is present at a concentration of about 1 mole percent to about 50 mole percent.

14. The polyoxazoline-phospholipid conjugate of claim 12, wherein vesicle forming lipid is a phospholipid.

15. The polyoxazoline-phospholipid conjugate of claim 12, further comprising a target molecule.

16. The polyoxazoline-phospholipid conjugate of claim 15, wherein the target molecule is linked to the polyoxazoline-phospholipid conjugate or entrapped within the liposome.

17. The polyoxazoline-phospholipid conjugate of claim 15, wherein the target molecule is an organic small molecule, an oligonucleotide, a polypeptide, an antibody, an antibody fragment, a protein, or a carbohydrate.

18. The polyoxazoline-phospholipid conjugate of claim 15, wherein the target molecule is a targeting agent, a diagnostic agent or a therapeutic agent.

19. The polyoxazoline-phospholipid conjugate of claim 15, wherein the target molecule is exposed to the extra-liposomal environment.

* * * * *